(12) United States Patent
Thota et al.

US007569580B2

(10) Patent No.: US 7,569,580 B2
(45) Date of Patent: Aug. 4, 2009

(54) HETEROTRICYCLIC COMPOUNDS FOR USE AS HCV INHIBITORS

(75) Inventors: Sambaiah Thota, Fremont, CA (US); Rajinder Singh, Belmont, CA (US); Guy Laidig, Menlo Park, CA (US); Henry Lu, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 469 days.

(21) Appl. No.: 11/145,144

(22) Filed: Jun. 3, 2005

(65) Prior Publication Data

US 2005/0282850 A1 Dec. 22, 2005

Related U.S. Application Data

(60) Provisional application No. 60/576,535, filed on Jun. 3, 2004, provisional application No. 60/576,521, filed on Jun. 3, 2004, provisional application No. 60/645,212, filed on Jan. 18, 2005.

(51) Int. Cl.
*A61K 31/4365* (2006.01)
*C07D 495/12* (2006.01)
(52) U.S. Cl. ........................................ 514/293; 546/83
(58) Field of Classification Search ................. 514/293; 546/83
See application file for complete search history.

(56) References Cited

U.S. PATENT DOCUMENTS

| 4,000,151 | A | | 12/1976 | Hester, Jr. | |
|---|---|---|---|---|---|
| 4,581,455 | A | * | 4/1986 | Wright | ........................ 546/83 |
| 2004/0048882 | A1 | | 3/2004 | Angibaud et al. | |
| 2004/0082592 | A1 | | 4/2004 | Mabire et al. | |
| 2005/0090521 | A1 | | 4/2005 | Thota et al. | |
| 2007/0149520 | A1 | | 6/2007 | Thota et al. | |

FOREIGN PATENT DOCUMENTS

| DE | 2206012 | 8/1972 |
|---|---|---|
| EP | 0 120 484 | 10/1984 |
| EP | 1162196 | 12/2001 |
| GB | 1 374 369 A | 11/1974 |
| WO | WO95/26348 | 10/1995 |
| WO | WO97/48704 | 12/1997 |
| WO | WO2002/28837 | 4/2002 |
| WO | WO2003/007945 | 1/2003 |
| WO | WO2003/040112 | 5/2003 |
| WO | WO2003/064456 | 8/2003 |
| WO | WO2005/0307774 | 4/2005 |

OTHER PUBLICATIONS

Yanborosova et al., Preparation and pharmacological activity of amides of 2-hydrazocinchoninic, 1,2,4-triazolo [4,3-a]-, and 1,2,3,4-tetrazolo[4,3-a]quinoline-9-carboxylic acids, Khimiko-Farmatsevticheskaya Zhurnal 30(3): 52-53 (1996).

Stn results, Document No.: 125:75750, Registry No.(s): 136354-35-6, 178533-22-7, 178533-23-8, 178533-24-9, 178533-25-0, 178533-26-1, and 178533-27-2.
Filer, C.N. et al., "Isoquinolines.8.Ethylene Oxide Mediated Conversion of Isoquinolines to Isoquinolones and Oxazolidines. Its Extension to Related Nitrogen Heterocycles", J. Org. Chem., vol. 44, No. 2, 1979 pp. 285-287.
Van Nispen, Simon et al., "Use of Dilithio-Tosylmethyl Isocyanide in the Synthesis of Oxazoles and Imidazoles", Tetrahedron Letters, vol. 21, pp. 3723-3726.
Tominaga, Yoshinori et al., "Polarized Ethylene. V. Synthesis of 1-Substituted Indolizine, Pyrazolo[1,5-a]pyridine, and Their Related Compounds Using Methoxyethylene Derivatives", Journal of Heterocyclic Chemistry, vol. 27, No. 263, 1990, pp. 263-268.
Roberts, Edward M. et al., "A Synthesis of 5,6-Benzopyrrocoline", Journal of Organic Chemistry, American Chemical Society, vol. 20, 1955, pp. 1443-1447.
Smith, R.M. et al., "Structure-Based Design of Hepatitis C Virus Inhibitors", Journal of Viral Hepatitis, vol. 10, 2003, pp. 405-412.
Invitation to Pay Additional Fees, PCT International Application No. PCT/US2005/019499, Aug. 3, 2006.
Mukherjee et al., "Synthesis and Bioevaluation of Substituted Dihydropyridines for Pregnancy-Interceptive Activity in Hamsters" J. Med. Chem., 32(10):2297-2300 (1989).
Meth-Cohn et al., "A Versatile New Synthesis of Quinolines and Related Fused Pyridines," Journal of the Chemical Society, Perkin Transactions 1: Organic and Bio-Organic Chemistry, 9:2509-2517 (1981).
McGaw, What it Means When an Examiner Says "Election of Species Requirement", Smith & Hopen, Article ID: 37 (2005).
Database Beilstein XP002313584, Database accession No. Beilstein Registry No.: 13090-43-2, S-triazolo '1, 5-alauinoline & Heterocycles vol. 31, No. 2, 1990, pp. 289-304.
Tetrahedron, vol. 54, 1998, pp. 3913-3918, XP002313579, compound 7.
Caplus Accession No. 1996: 464309.
Stadbauer, et al., "Study of the Thermal Behavior of Azidohetarenes with Differential Scanning Calorimetry", Journal of Biochemical and Biophysical Methods, (2002), vol. 53, 89-99.
Caplus Accession No. 1994: 533294.
Caplus Accession No. 1993: 551632.
Caplus Accession No. 1990: 138965.
Caplus Accession No. 1986: 583403.
Caplus Accession No. 1986: 442681.
Search Report for PCT/US2004/031705 dated Feb. 2, 2005.
STN International Search Report, 39 pages.

* cited by examiner

*Primary Examiner*—Charanjit S Aulakh
(74) *Attorney, Agent, or Firm*—McDonnell Boehnen Hulbert & Berghoff LLP

(57) ABSTRACT

The present invention comprises tetrazoloquinoline-compounds that are inhibitors of HCV. Compositions comprising the compounds in combination with a pharmaceutically acceptable carrier are also disclosed, as are methods of using the compounds and compositions to inhibit HCV infection of a cell, particular in the form of treating HCV infection in a mammal.

11 Claims, No Drawings

HETEROTRICYCLIC COMPOUNDS FOR USE AS HCV INHIBITORS

CROSS REFERENCE TO RELATED APPLICATIONS

This application claims priority from U.S. Provisional Patent Application No. 60/645,212, filed on Jan. 18, 2005, from U.S. Provisional Patent Application No. 60/576,535, filed on Jun. 3, 2004, and from U.S. Provisional Patent Application No. 60/576,521, filed on Jun. 3, 2004.

FIELD OF THE INVENTION

The present invention is in the field of small molecule inhibitors of HCV and methods of using them to inhibit HCV.

SUMMARY OF THE RELATED ART

The hepatitis C virus (HCV) is one of the most important causes of chronic liver disease in the United States. It accounts for about 15 percent of acute viral hepatitis, 60 to 70 percent of chronic hepatitis, and up to 50 percent of cirrhosis, end-stage liver disease, and liver cancer. Almost 4 million Americans, or 1.8 percent of the U.S. population, have antibody to HCV (anti-HCV), indicating ongoing or previous infection with the virus. Hepatitis C causes an estimated 8,000 to 10,000 deaths annually in the United States.

A distinct and major characteristic of hepatitis C is its tendency to cause chronic liver disease. At least 75 percent of patients with acute hepatitis C ultimately develop chronic infection, and most of these patients have accompanying chronic liver disease.

Chronic hepatitis C varies greatly in its course and outcome. At one end of the spectrum are patients who have no signs or symptoms of liver disease and completely normal levels of serum liver enzymes. Liver biopsy usually shows some degree of chronic hepatitis, but the degree of injury is usually mild, and the overall prognosis may be good. At the other end of the spectrum are patients with severe hepatitis C who have symptoms, HCV RNA in serum, and elevated serum liver enzymes, and who ultimately develop cirrhosis and end-stage liver disease. In the middle of the spectrum are many patients who have few or no symptoms, mild to moderate elevations in liver enzymes, and an uncertain prognosis. Researchers estimate that at least 20 percent of patients with chronic hepatitis C develop cirrhosis, a process that takes 10 to 20 years. After 20 to 40 years, a smaller percentage of patients with chronic disease develop liver cancer. The therapy of chronic hepatitis C has evolved steadily since alpha interferon was first approved for use in this disease more than ten years ago. At the present time, the optimal regimen appears to be a 24- or 48-week course of the combination of pegylated alpha interferon and ribavirin.

Two forms of peg-interferon have been developed and studied in large clinical trials: peg-interferon alfa-2a (Pegasys®: Hoffman La Roche: Nutley, N.J.) and peg-interferon alfa-2b (Pegintron®: Schering-Plough Corporation, Kenilworth, N.J.). These two products are roughly equivalent in efficacy and safety, but have different dosing regimens. Peg-interferon alfa-2a is given subcutaneously in a dose of 180 mcg per week. Peg-interferon alfa-2b is given subcutaneously weekly in doses of 1.5 mcg per kilogram per week (thus in the range of 75 to 150 mcg per week).

Ribavirin is an oral antiviral agent that has activity against a broad range of viruses. By itself, ribavirin has little effect on HCV, but adding it to interferon increases the sustained response rate by two- to three-fold. For these reasons, combination therapy is now recommended for hepatitis C and interferon monotherapy is applied only when there are specific reasons not to use ribavirin.

Ribavirin is an oral medication, given twice a day in 200-mg capsules for a total daily dose of 800 to 1,200 mg based upon body weight and the form of peg-interferon. When combined with peg-interferon alfa-2b, the recommended dose of ribavirin is 800 mg per day. When combined with peg-interferon alfa-2a, the dose of ribavirin is 1,000 mg for patients who weigh less than 75 kilograms (165 pounds) and 1,200 mg for those who weight more than 75 kilograms. In all situations, ribavirin is given in two divided doses daily.

At the present, peg-interferon alfa-2a has not been approved for use in chronic hepatitis C in the United States and is available only in clinical trials. Thus, only peg-interferon alfa-2b is available for general use.

Combination therapy leads to rapid improvements in serum ALT levels and disappearance of detectable HCV RNA in up to 70 percent of patients. However, long-term improvement in hepatitis C occurs only if HCV RNA disappears during therapy and stays undetectable once therapy is stopped. Among patients who become HCV RNA negative during treatment, a proportion relapse when therapy is stopped. The relapse rate is lower in patients treated with combination therapy compared with monotherapy. Thus, a 48-week course of combination therapy using peg-interferon and ribavirin yields a sustained response rate of approximately 55 percent. A similar course of peg-interferon monotherapy yields a sustained response rate of only 35 percent. A response is considered "sustained" if HCV RNA remains undetectable for six months or more after stopping therapy.

The optimal duration of treatment varies depending on whether interferon monotherapy or combination therapy is used, as well as by HCV genotype. For patients treated with peg-interferon monotherapy, a 48-week course is recommended, regardless of genotype. For patients treated with combination therapy, the optimal duration of treatment depends on viral genotype. Patients with genotypes 2 and 3 have a high rate of response to combination treatment (70 to 80 percent), and a 24-week course of combination therapy yields results equivalent to those of a 48-week course. In contrast, patients with genotype 1 have a lower rate of response to combination therapy (40 to 45 percent), and a 48-week course yields a significantly better sustained response rate. Again, because of the variable responses to treatment, testing for HCV genotype is clinically useful when using combination therapy.

In view of the foregoing, there is a desire for alternative, more effective agents for treating HCV infection.

SUMMARY OF THE INVENTION

The invention provides compounds and methods for treating HCV infection. The invention provides new inhibitors of HCV.

In a first aspect, the invention provides compounds that are useful as inhibitors of HCV.

In a second aspect, the invention provides a composition comprising an inhibitor of HCV according to the invention and a pharmaceutically acceptable carrier, excipient, or diluent.

In a third aspect, the invention provides a method of inhibiting HCV in a cell, comprising contacting a cell in which inhibition of HCV is desired with an inhibitor of HCV of the invention.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The Embodiment 1 of the invention comprises compounds of formulae I or II,

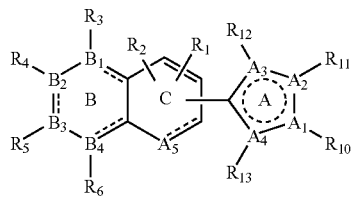

I

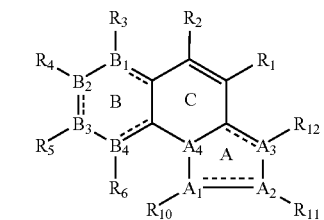

II and pharmaceutically acceptable salts, hydrates, solvates and N-oxides thereof wherein, $R_1$ is hydrogen, —OH, $C_1$-$C_6$-alkyl, heterocyclyl, $C_1$-$C_6$-alkyl-$OR_7$, $C_1$-$C_6$-alkyl-OH, aryl, heteroaryl, heterocyclic, halogen, cyano, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—$N(R_7)$—$OR_7$, —CO—$R_7$, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —$SO_2R_7$, —$SOR_7$, —$SO_2NH_2$, —$SO_2NHR_7$, —$SO_2NR_7R_7$, —$SO_2$-heteroaryl, —$SO_2$-aryl, —$SO_3H$, —$SO_3R_7$, —$SO_2Cl$, —$NHR_7$, $C_1$-$C_6$alkyl-NH($R_7$)-aryl, $C_1$-$C_6$-alkyl-$NR_7$—$OR_7$, —NH($R_7$)— aryl, —CO-heteroaryl, —NH—CO—O—$R_7$-aryl, —NH—CO—NH—$SO_2$-aryl, —NH—CO—$OR_7$, —NH—CO—NH—($C_1$-$C_6$-alkyl) or —NH—CO—($C_1$-$C_6$-alkyl), wherein each of the alkyl, heterocyclyl, heteroaryl and aryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

each of $R_2$, $R_3$, $R_4$, $R_5$ and $R_6$ is independently selected from hydrogen, nitro, —OH, $C_1$-$C_6$-alkyl, heterocyclyl, —O-halo($C_1$-$C_6$-alkyl), halo($C_1$-$C_6$-alkyl), $C_1$-$C_6$-alkyl-$OR_7$, $C_1$-$C_6$-alkyl-OH, aryl, heteroaryl, heterocyclic, halogen, cyano, —$OCF_3$, —$CF_3$, azido, —O—($C_3$-$C_6$-cycloalkyl), —S—($C_1$-$C_6$-alkyl), $C_1$-$C_6$-alkoxy, —($C_1$-$C_6$-alkoxy)-aryl, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—$N(R_7)$—$OR_7$, —CO—$R_7$, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —$SO_2R_7$, —$SOR_7$, —$SO_2NH_2$, —$SO_2NHR_7$, —$SO_2NR_7R_7$, —$SO_2$-heteroaryl, —$SO_2$-aryl, —$SO_3H$, —$SO_3R_7$, —$SO_2Cl$, —$NH_2$, —$NHR_7$, —$NR_7R_7$, $C_1$-$C_6$alkyl-NH($R_7$)- aryl, $C_1$-$C_6$-alkyl-$NR_7$—$OR_7$, —NH($R_7$)-aryl, —CO-heteroaryl, —N($R_7$)—CO—$R_7$, —NH—$SO_2$—$R_7$, —N($R_7$)—CO—$NR_7R_7$, —NH—CO—O—$R_7$-aryl, —NH—CO—NH—$SO_2$-aryl, —$NR_7$—CO—$OR_7$, —NH—CO—$OR_7$, —NH—CO—NH—($C_1$-$C_6$-alkyl) or —NH—CO—($C_1$-$C_6$-alkyl), wherein each of the alkyl, heterocyclyl, heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen; or any adjacent two of $R_3$, $R_4$, $R_5$ and $R_6$ together with the carbon atoms to which they are attached form an aryl, heterocyclyl or heteroaryl; or $R_1$ and $R_2$ are independently H or a group selected from

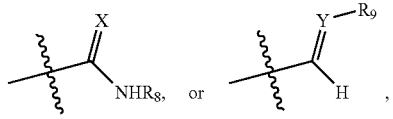

wherein X is =NH or =S, Y is =N—, $R_8$ is hydrogen or hydroxy, $R_9$ is hydroxy, $C_1$-$C_6$-alkoxy or aryl optionally substituted with hydroxy or $C_1$-$C_6$-alkyl; or when adjacent, optionally $R_1$ and $R_2$ together with the carbon atoms to which they are attached form a mono or bicyclic aryl or heteroaryl;

each of $R_{10}$, $R_{11}$, $R_{12}$ and $R_{13}$ is independently selected from hydrogen, —CN, —$NO_2$, —OH, $C_1$-$C_6$-alkyl, aryl, $C_1$-$C_6$-alkyl-aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—$R_7$, —CO—OH, —CO—$OR_7$, —CO—$NH_2$, —CO—$NHR_7$, —CO—$NR_7R_7$, —CO—$N(R_7)OR_7$, —CO—$NR_7OH$, —CO—$NHOR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —CO—$N(R_7)OH$, —CO—NHOH, —CO—H, —$SO_2$—$R_7$, —SO—$R_7$, —SO—($C_1$-$C_6$-alkyl), —$SO_2$—($C_1$-$C_6$-alkyl), —$SO_2NH_2$, —$SO_2NHR_7$, —$SO_2NR_7R_7$, —CO-heteroaryl, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, —$NH_2$, —$NHR_7$, —$NR_7R_7$, —$N(R_7)$—CO—$R_7$, —$NHSO_2R_7$, —$N(R_7)$—CO—$OR_7$ or —$N(R_7)$—CO—$NR_7R_7$, or when the annular B ring atom to which it is bound is N, $R_3$ is optionally absent, wherein each of the alkyl, alkoxy, aryl, heteroaryl and heterocyclyl are optionally substituted with one or more halogen, $C_1$-$C_6$-alkyl, $C_1$-$C_6$-alkoxy, —$OCF_3$, —$CF_3$, —CN, —$NH_2$, —$NO_2$, —OH, mono- or di-$C_1$-$C_6$-alkylamino, or oxo;

$R_7$ is hydrogen, a pro-drug group, $C_0$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

$A_1$, $A_2$, $A_3$, and $A_4$ are independently carbon, oxygen, nitrogen, sulfur, —S(O)—, —S($O_2$)—, —C(O)—, or —N(R₇)—, wherein when A₁ and A₂ are carbon, then the group formed by A₁, A₂ together with R₁₀ and R₁₁ is not phenyl;

A₅ is carbon or nitrogen;

B₁, B₂, B₃, and B₄ are independently a covalent bond, C, O, —S(O)₀₋₂— or N, wherein when one of B₁, B₂, B₃, and B₄ is a covalent bond the R group attached to it is absent and the B ring is a five membered ring, and when B is O, —S(O)₀₋₂— or N then the R group attached is absent; and the dashed lines of rings A, B and C represent single or double bonds such that each annular N has three bonds, each annular O has two bonds, each annular S has two bonds and each annular C has four bonds; annular sulfur atoms may exist as sulfide, sulfoxide and sulfone oxidation states;

provided at least one of B₁, B₂, B₃ and B₄ of Formula II is a heteroatom.

In Embodiment 2, the invention provides compounds according to Formulae I and II, wherein B₁ to B₄ are carbon atoms, provided that when the compounds are according to Formulae II and A₁, A₂, A₃ and A₄ are N, then R₁ to R₆ and R₁₀ to R₁₂ are not all hydrogen;

when R₂ to R₆ are hydrogen, R₁ is not —CH₃, —CO-phenyl, —CO—H or chloro;

when R₁ and R₃ to R₆ are hydrogen, R₂ is not bromo, —CH₂—OH, cyano, iodo, —CO—OH, —CH₃, —CH₂OCH₃, morpholino, —CH₂NH—CH₂CH₃, vinyl, —CH₂CH₃, chloro, —CH₂NH₂ or azido;

when R₁ to R₃ and R₅ to R₆ are hydrogen, R₄ is not chloro, ethynyl or —CH₃;

when R₁ to R₄ and R₆ are hydrogen, R₅ is not —CH₃ or —CH₂NH-isopropyl;

when R₁ to R₅ are hydrogen, R₆ is not —CH₂Br, chloro, —CH₃, —CH₂—OH, —CO—H, —NO₂, —NH₂, acetamido, —CH₂OCH₃, —CH₂—CN, propyl, iodo or —CH₂OCH₂CH₃; and the compounds of formula II are not one of the following combinations when B₁-B₄ are all C:

Embodiment 3 comprises compounds according to formula II

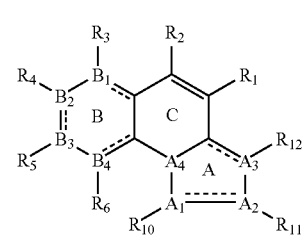

and pharmaceutically acceptable salts, hydrates, solvates and N-oxides thereof wherein $R_1$ and $R_2$ are independently hydrogen, —OH, $C_1$-$C_6$-alkyl, $C_1$-$C_6$-alkyl-OR₇, $C_1$-$C_6$-alkyl-OH, aryl, heteroaryl, halogen, —CO—H, —CO—OH, —CO—OR₇, —CO—NH₂, —CO—NHR₇, —CO—NR₇R₇, —CO—NH—OH, —CO—NH—OR₇, —CO—NR₇—OH, —CO—N(R₇)—OR₇, —CO—R₇, $C_1$-$C_6$-alkyl-NH—OR₇, $C_1$-$C_6$-alkyl-NH—OH, $C_1$-$C_6$-alkyl-NR₇—OH, $C_1$-$C_6$-alkyl-NR₇—OR₇, $C_1$-$C_6$-alkyl-CO—NHOR₇, $C_1$-$C_6$-alkyl-CO—NR₇OR₇, $C_1$-$C_6$-alkyl-CO—NHOH, $C_1$-$C_6$-alkyl-CO—NR₇OH, —SO₂R₇, —SOR₇, —SO₂NH₂, —SO₂NHR₇, —SO₂NR₇R₇, —SO₂heteroaryl, —SO₂-aryl, —SO₃H, —SO₃R₇, —SO₂Cl, —SO₂NHR₇, —SO₂N(R₇), —NHR₇, $C_1$-$C_6$alkyl-NH(R₇)-aryl, $C_1$-$C_6$-alkyl-NR₇—OR₇, —NH(R₇)-aryl, —CO-heteroaryl, —NH—CO—O—R₇-aryl, —NH—CO—NH—SO₂-aryl, —NH—CO—OR₇, —NH—CO—NH—($C_1$-$C_6$-alkyl) or —NH—CO—($C_1$-$C_6$-alkyl), wherein each of the alkyl, heterocyclyl, heteroaryl and aryl groups are optionally substituted with

| A₁ | A₂ | A₃ | A₄ | R₁ | R₂ | R₃ | R₄ | R₅ | R₆ |
|---|---|---|---|---|---|---|---|---|---|
| N | N | N | N | —CO—H | —H | —H | —H | —CH₃ | —H |
| N | N | N | N | —CO—OH | —H | —H | —N₃ | —N₃ | —H |
| N | N | N | N | —CO—OH | —H | —H | —OCH₃ | —OCH₃ | —H |
| N | N | N | N | —H | —CH₃ | —H | —H | —OCH₃ | —H |
| N | N | N | N | —CN | piperidyl | —H | —H | —H | —H |
| C | N | N | N | —H | —CH₃ or —H | —H | —H | —H | —H |
| N | N | N | N | —H | —CH₃ | —H | —H | —H | —F or —Br |
| N | N | N | N | —CN, —CH₃ or —CH₂CH₃ | —Cl | —H | —H | —H | —H |
| N | N | N | N | —H | —Cl | —H | —CH₃ | —H | —H |
| N | N | N | N | —H | —Cl | —H | —H | —H | —CH₃, —Cl, —F, or —CH₂NHCH₃ |
| N | N | N | N | —H | —N₃ or —CH₃ | —H | —CH₃ | —H | —H |
| N | N | N | N | —H | —N₃ | —H | —H | —H | —Cl |
| N | N | N | N | —H | —CH₂Cl | —H | —H | —H | —CH₂Cl |
| N | N | N | N | —CH₃ | —Cl | —H | —H | —H | —Cl, —F or —CH₃ |
| N | N | N | N | —H | —Cl | —Cl | —H | —H | —Cl |
| N | N | N | N | —H | —CH₃ | —H | —H | —H | —CH₃, —CH₂CH₃ or —Cl |
| N | N | N | N | —H | —CH₃ | —H | —CH₂CH₃ | —H | —H |
| N | N | N | N | —H | morpholino | —H | —Cl | —H | —Cl |
| N | N | N | N | —H | —CH₃ | —H | —Cl | —H | —H |
| N | N | N | N | —Cl | —CH₃ | —H | —H | —H | —H |

$C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen; or one of $R_1$ or $R_2$ is H and the other is

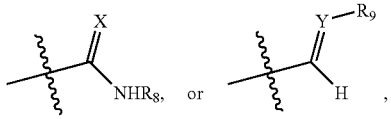

wherein X is =NH or =S, Y is =N—, $R_8$ is hydrogen or hydroxy, $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

$R_3$, $R_4$, $R_5$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), —SO—($C_1$-$C_6$-alkyl), —SO$_2$—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —CO—NHOH, —CO—NHOR$_7$, —CO—NR$_7$OH, —CO—NR$_7$OR$_7$, —SO$_2$—($C_1$-$C_6$-alkyl), —SO$_2$NH$_2$, —SO$_2$NHR$_7$, —SO$_2$NR$_7$R$_7$, —SO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$, —N(R$_7$)—CO—NR$_7$R$_7$, or, when the annular B ring atom to which it is bound is N, $R_3$-$R_6$ is optionally absent; or $R_4$ and $R_5$ together with the carbon atoms to which they are attached form a heteroaryl;

$R_7$ is hydrogen, a pro-drug group, $C_0$-$C_6$-alkyl, —($C_1$-$C_6$-alkyl)-OH, —($C_1$-$C_6$-alkyl)-O—($C_1$-$C_6$-alkyl), —(C1—$C_6$-alkyl)-CN, $C_2$-$C_6$-alkene, heterocyclyl, aryl, heteroaryl or $C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

$R_{10}$, $R_{11}$, and $R_{12}$ are independently hydrogen, —CN, —NO$_2$, —OH, $C_1$-$C_6$-alkyl, aryl, $C_1$-$C_6$-alkyl-aryl, —O-halo($C_1$-$C_6$-alkyl), halo($C_1$-$C_6$-alkyl), —O—($C_3$-$C_6$-cycloalkyl), —S—($C_1$-$C_6$-alkyl), —SO—($C_1$-$C_6$-alkyl), —SO$_2$—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—R$_7$, —CO—OH, —CO—OR$_7$, —CO—NH$_2$, —CO—NHR$_7$, —CO—NR$_7$R$_7$, —CO—N(R$_7$)OR$_7$, —CO—NHOR$_7$, $C_1$-$C_6$-alkyl-CO—NHOR$_7$, $C_1$-$C_6$-alkyl-CO—NR$_7$OR$_7$, $C_1$-$C_6$-alkyl-CO—NHOH, $C_1$-$C_6$-alkyl-CO—NR$_7$OH, —CO—N(R$_7$)OH, —CO—NHOH, —CO—H, —SO$_2$—R$_7$, —SO—R$_7$, —SO$_2$—($C_1$-$C_6$-alkyl), —SO$_2$NH$_2$, —SO$_2$NHR$_7$, —SO$_2$NR$_7$R$_7$, —CO-heteroaryl, $C_1$-$C_6$-alkyl-NH—OR$_7$, $C_1$-$C_6$-alkyl-NH—OH, $C_1$-$C_6$-alkyl-NR$_7$—OH, $C_1$-$C_6$-alkyl-NR$_7$—OR$_7$, —NH$_2$, —NHR$_7$, —NR$_7$R$_7$, —N(R$_7$)—CO—R$_7$, —NHSO$_2$R$_7$, —N(R$_7$)—CO—OR$_7$ or —N(R$_7$)—CO—NR$_7$R$_7$, wherein each of the alkyl, alkoxy, aryl, heteroaryl and heterocyclyl are optionally substituted with one or more halogen, $C_1$-$C_6$-alkyl, $C_1$-$C_6$-alkoxy, —OCF$_3$, —CF$_3$, —CN, —NH$_2$, —NO$_2$, —OH, mono- or di-$C_1$-$C_6$-alkylamino, or oxo;

$A_1$, $A_2$, and $A_3$ are independently carbon, oxygen, nitrogen, sulfur, —S(O)—, —S(O$_2$)—, —C(O)—, or —N(R$_7$)—;

$A_4$ is carbon or nitrogen;

$B_1$, $B_2$, $B_3$, and $B_4$ are independently a covalent bond, C, O, —S(O)$_{0\text{-}2}$— or N, wherein when one of $B_1$, $B_2$, $B_3$, and $B_4$ is a covalent bond the R group attached to it is absent and the B ring is a five membered ring; and the dashed lines of rings B and A represent single or double bonds such that each annular N has three bonds, each annular O has two bonds, each annular S has two bonds and each annular C has four bonds; annular sulfur atoms may exist as sulfide, sulfoxide and sulfone oxidation states; provided at least one of $B_1$, $B_2$, $B_3$ and $B_4$ is a heteroatom.

Embodiment 3a of the invention comprises compounds according to formula II wherein one of $B_1$, $B_2$, $B_3$, and $B_4$ is a covalent bond, and another is S and the remaining two are C, wherein the dashed lines of ring B are independently single or double bonds such that the annular S has two bonds and each annular C has four bonds; $A_1$, $A_2$, $A_3$ and $A_4$ are independently carbon or nitrogen; $R_2$ to $R_6$ and $R_{10}$ to $R_{12}$ are hydrogen; $R_1$ is

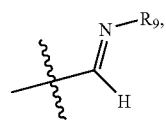

wherein $R_9$ is hydroxy or $C_1$-$C_3$-alkoxy, —CO—H, —CO—OH, —CO—NH—OH, or —CO—NH—OR$_7$, wherein $R_7$ is a heterocyclyl, wherein the heterocyclyl groups is optionally substituted with $C_1$-$C_6$-alkyl, hydroxy, $C_1$-$C_6$-alkoxy, cyano, or halogen.

Embodiment 3b comprises compounds according to Embodiment 3a wherein $A_1$ to $A_4$ are nitrogen. Preferably, the compound according to Embodiment 3b comprises compounds wherein $B_1$ is S, $B_2$ and $B_3$ are C and $B_4$ is a covalent bond. Preferably, $R_9$ is methoxy. Also preferred are compounds according to Embodiment 3a wherein the heterocyclyl is pyranyl, preferably, pyran-2-yl.

Illustrative, but non-limiting, examples of the B ring include (where the bonds in bold are shared with the C ring):

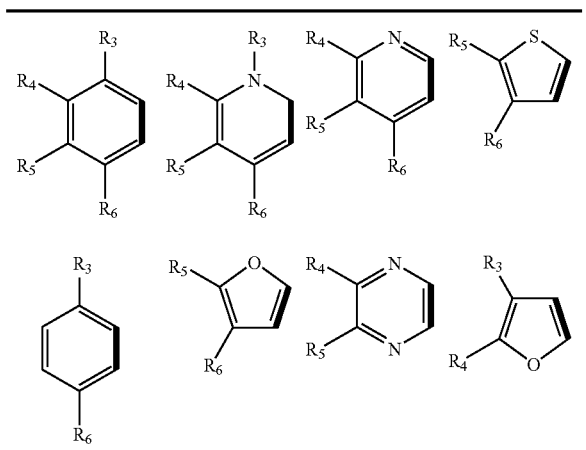

-continued

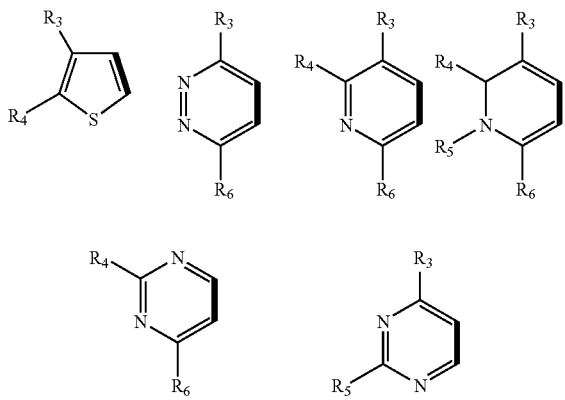

The following table presents preferred embodiments of $B_1$-$B_4$:

| $B_1$ | $B_2$ | $B_3$ | $B_4$ | $B_1$ | $B_2$ | $B_3$ | $B_4$ | $B_1$ | $B_2$ | $B_3$ | $B_4$ |
|---|---|---|---|---|---|---|---|---|---|---|---|
| C | C | N | N | C | C | N | C | N | C | C | N |
| C | C | C | C | C | C | C | N | C | N | C | N |
| N | C | C | C | N | N | C | C | C | C | N | N |
| C | N | C | C | N | C | N | C | | | | |

Embodiment 4 comprises compounds according to Embodiment 3 of the formula

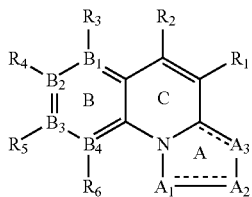

III and pharmaceutically acceptable salts, hydrates, solvates and N-oxides thereof wherein $R_1$ and $R_2$ are independently hydrogen, $C_1$-$C_6$-alkyl, heterocyclic, $C_1$-$C_6$-alkyl-OH, aryl, heteroaryl, halogen, cyano, —CO—H, —CO—OH, —CO—OR$_7$, —CO—NH$_2$, —CO—NHR$_7$, —CO—NR$_7$R$_7$, —CO—NH—OH, —CO—NH—OR$_7$, —CO—N(R$_7$)—OR$_7$, —CO—R$_7$, —SO$_2$NH$_2$, —SO$_2$NHR$_7$, —SO$_2$NR$_7$R$_7$, —SO$_2$-heteroaryl, —SO$_2$-aryl, —SO$_3$H, —NHR$_7$, $C_1$-$C_6$-alkyl-NH(R$_7$)-aryl, —NH(R$_7$)-aryl, —CO-heteroaryl, —NH—CO—O—R$_7$-aryl, —NH—CO—NH—SO$_2$-aryl, —NH—CO—OR$_7$, —NH—CO—NH—(C$_1$-C$_6$-alkyl) or —NH—CO—(C$_1$-C$_6$-alkyl), wherein each of the heteroaryl and aryl groups are optionally substituted with $C_1$-$C_6$-alkyl, nitro, hydroxy, $C_1$-$C_6$-alkoxy, —CO—O—(C$_1$-C$_6$-alkyl), cyano, —O-halo(C$_1$-C$_6$-alkyl), halo(C$_1$-C$_6$-alkyl) or halogen; or $R_1$ or $R_2$ is a group selected from

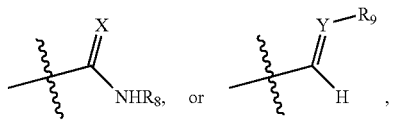

wherein $R_8$ is hydrogen or hydroxy; X is =NH or =S, Y is =N—, and $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

$R_3$, $R_4$, $R_5$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_3$H, —SO$_2$-(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

$R_4$ and $R_5$ together with the carbon atoms to which they are attached form a heteroaryl;

$R_7$ is hydrogen, $C_0$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

$A_1$, $A_2$ and $A_3$ are independently carbon, oxygen, or nitrogen; and ring B contains 1 or 2 nitrogen atoms;

Embodiment 5 comprises compounds according to Embodiment 4 of the formula

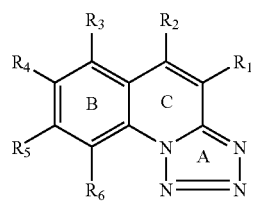

IV or a pharmaceutically acceptable salt thereof wherein $R_1$ and $R_2$ are independently hydrogen, $C_1$-$C_6$-alkyl, heterocyclic, $C_1$-$C_6$-alkyl-OH, aryl, heteroaryl, halogen, cyano, —CO—H, —CO—OH, —CO—OR$_7$, —CO—NH$_2$, —CO—NHR$_7$, —CO—NR$_7$R$_7$, —CO—NH—OH, —CO—NH—OR$_7$, —CO—N(R$_7$)—OR$_7$, —CO—R$_7$, —SO$_3$H, —SO$_2$NH$_2$, —SO$_2$NHR$_7$, —SO$_2$NR$_7$R$_7$, —SO$_2$-heteroaryl, —SO$_2$-aryl, —NHR$_7$, $C_1$-$C_6$-alkyl-NH(R$_7$)-aryl, —NH(R$_7$)-aryl, —CO-heteroaryl, —NH—CO—O—R$_7$-aryl, —NH—CO—NH—SO$_2$-aryl, —NH—CO—OR$_7$, —NH—CO—NH—(C$_1$-C$_6$-alkyl) or —NH—CO—(C$_1$-C$_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen; or $R_1$ or $R_2$ is a group selected from

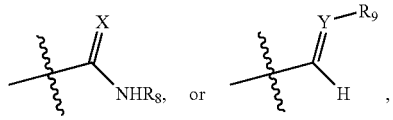

wherein $R_8$ is hydrogen or hydroxy; X is =NH or =S; Y is =N—, and $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

$R_3$, $R_4$, $R_5$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—($C_1$-$C_6$-alkyl), —SO$_3$H, —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

$R_4$ and $R_5$ together with the carbon atoms to which they are attached form a heteroaryl;

$R_7$ is hydrogen, $C_0$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen; and provided that:

$R_1$ to $R_6$ are not all hydrogen;

when $R_2$ to $R_6$ are hydrogen, $R_1$ is not —CO-phenyl, —CO—H or chloro;

when $R_1$ and $R_3$ to $R_6$ are hydrogen, $R_2$ is not bromo, —CH$_2$—OH, cyano, iodo, —CO—OH, —CH$_3$, —CH$_2$OCH$_3$, morpholino, —CH$_2$NH—CH$_2$CH$_3$, vinyl, —CH$_2$CH$_3$, chloro, —CH$_2$NH$_2$ or azido;

when $R_1$ to $R_3$ and $R_5$ to $R_6$ are hydrogen, $R_4$ is not chloro, ethynyl or —CH$_3$;

when $R_1$ to $R_4$ and $R_6$ are hydrogen, $R_5$ is not —CH$_3$ or —CH$_2$NH-isopropyl;

when $R_1$ to $R_5$ are hydrogen, $R_6$ is not —CH$_2$Br, chloro, —CH$_3$, —CH$_2$—OH, —CO—H, —NO$_2$, —NH$_2$, acetamido, —CH$_2$OCH$_3$, —CH$_2$—CN, propyl, iodo or —CH$_2$OCH$_2$CH$_3$; and the compounds of formula IV are not one of the following combinations

| $R_1$ | $R_2$ | $R_3$ | $R_4$ | $R_5$ | $R_6$ |
|---|---|---|---|---|---|
| —CO—H | —H | —H | —H | —CH$_3$ | —H |
| —CO—OH | —H | —H | —N$_3$ | —N$_3$ | —H |
| —CO—OH | —H | —H | —OCH$_3$ | —OCH$_3$ | —H |
| —H | —CH$_3$ | —H | —H | —OCH$_3$ | —H |
| —CN | piperidyl | —H | —H | —H | —H |

-continued

| $R_1$ | $R_2$ | $R_3$ | $R_4$ | $R_5$ | $R_6$ |
|---|---|---|---|---|---|
| —H | —CH$_3$ or —H | —H | —H | —H | —H |
| —H | —CH$_3$ | —H | —H | —H | —F or —Br |

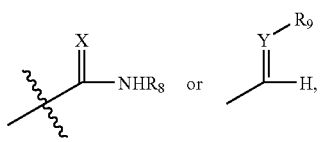

wherein $R_8$ is hydrogen or hydroxy, X is =N or =S, Y is =N—, and $R_9$ is hydroxy or $C_1$-$C_6$-alkoxy; $R_4$ and $R_5$ are independently selected from hydrogen, —S—($C_1$-$C_6$-alkyl), $C_1$-$C_6$-alkyl, —O—($C_3$-$C_6$-cycloalkyl), $C_1$-$C_6$-alkoxy, halogen, —SO$_2$—($C_1$-$C_6$-alkyl), heterocyclyl, —O-halo($C_1$-$C_6$-alkyl), halo($C_1$-$C_6$-alkyl), —NH$_2$ or together with the carbon atom to which they are attached form a heteroaryl group; $R_2$, $R_3$ and $R_6$ are hydrogen; and wherein the each of the aryl, heteroaryl and heterocyclyl groups are optionally substituted with —CO—O—($C_1$-$C_6$-alkyl), $C_1$-$C_6$-alkyl, nitro, hydroxy, $C_1$-$C_6$-alkoxy, cyano, —O-halo($C_1$-$C_6$-alkyl), halo($C_1$-$C_6$-alkyl) or halogen.

Embodiment 5 g of the invention comprises compounds according to formula IV wherein $R_1$ and $R_2$ are independently —NH(R$_7$)-aryl, —CO—OH, —CO—OR$_7$, $C_1$-$C_6$-alkyl, aryl or together with the carbon atoms to which they are attached form a bicyclic heteroaryl; $R_3$ to $R_6$ are hydrogen; and wherein each of the aryl and heteroaryl groups are optionally substituted with —CO—O—($C_1$-$C_6$-alkyl), $C_1$-$C_6$-alkyl, nitro, hydroxy, $C_1$-$C_6$-alkoxy, cyano, —O-halo($C_1$-$C_6$-alkyl), halo($C_1$-$C_6$-alkyl) or halogen.

Embodiment 5 h of the invention comprises compounds of formula IV wherein $R_1$ is —CO—OH, —CO—OR$_7$, or —CO—NH—OR$_7$; $R_6$ is $C_1$-$C_6$-alkyl, halogen, or —O—($C_1$-$C_6$-alkyl); and $R_2$ to $R_5$ are hydrogen.

Embodiment 5i of the invention comprises compounds according to formula IV wherein $R_1$ is —CO—OR$_7$; $R_3$ is azido or $C_1$-$C_6$-alkyl; and $R_2$, $R_4$ to $R_6$ are hydrogen.

Embodiment 6 comprises compounds according to formula I

I

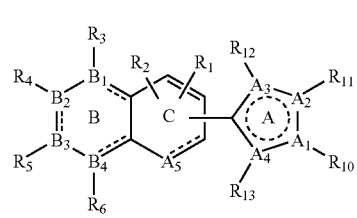

wherein $R_1$-$R_6$, $R_{10}$-$R_{13}$, $A_1$-$A_5$, and $B_1$-$B_5$ are as defined for Embodiment 1, above.

| $R_1$ | $R_2$ | $R_3$ | $R_4$ | $R_5$ | $R_6$ |
|---|---|---|---|---|---|
| —CN, —CH$_3$ or —CH$_2$CH$_3$ | —Cl | —H | —H | —H | —H |
| —H | —Cl | —H | —CH$_3$ | —H | —H |
| —H | —Cl | —H | —H | —H | —CH$_3$, —Cl, —F, or —CH$_2$NHCH$_3$ |
| —H | —N$_3$ or —CH$_3$ | —H | —CH$_3$ | —H | —H |
| —H | —N$_3$ | —H | —H | —H | —Cl |
| —H | —CH$_2$Cl | —H | —H | —H | —CH$_2$Cl |
| —CH$_3$ | —Cl | —H | —H | —H | —Cl, —F or —CH$_3$ |
| —H | —Cl | —Cl | —H | —H | —Cl |
| —H | —CH$_3$ | —H | —H | —H | —CH$_3$, —CH$_2$CH$_3$ or —Cl |
| —H | —CH$_3$ | —H | —CH$_2$CH$_3$ | —H | —H |
| —H | morpholino | —H | —Cl | —H | —Cl |
| —H | —CH$_3$ | —H | —Cl | —H | —H |
| —Cl | —CH$_3$ | —H | —H | —H | —H |

Embodiment 5a of the invention comprises compounds of formula IV wherein $R_1$ is —CO—NH—OR$_7$, $R_5$ is halogen, $R_2$ to $R_4$ and $R_6$ are hydrogen. More preferrably, $R_7$ is hydrogen and $R_5$ is chloro.

Embodiment 5b of the invention comprises compounds of formula IV wherein $R_1$ is aryl optionally substituted with one or more halo($C_1$-$C_6$-alkyl), cyano, —O-halo($C_1$-$C_6$-alkyl), or halogen, $R_5$ is halogen, $R_2$ to $R_4$ and $R_6$ are hydrogen. More preferably, the compounds are compounds wherein $R_1$ is phenyl optionally substituted with one or more —CF$_3$ or F and $R_5$ is chloro.

Embodiment 5c of the invention comprises compounds of formula IV wherein $R_1$ is —CO—NH—OR$_7$, Rr is halogen and $R_2$ to $R_5$ are hydrogen. Preferred compounds of this embodiment are compound wherein $R_7$ is isobutyl, propyl, isopropyl or ethyl and $R_6$ is chloro.

Embodiment 5d of the invention comprises compounds of formula IV wherein $R_1$ is —NH—CO—OR$_7$, $R_5$ is halogen, $R_2$ to $R_4$ and $R_6$ are hydrogen, preferably $R_7$ is tert-butyl and $R_5$ is chloro.

Embodiment 5e of the invention comprises compounds of formula IV wherein $R_1$ is —CO—OR$_7$, $R_6$ is halo($C_1$-$C_6$-alkyl) and $R_2$ to $R_5$ are hydrogen, preferably the compound are compounds wherein $R_7$ is hydrogen and $R_6$ is —CF$_3$.

Embodiment 5f of the invention comprises compounds of formula IV wherein $R_1$ is —NH—CO—NH—SO$_2$-aryl, —NH—CO—NH—($C_1$-$C_6$-alkyl), $C_1$-$C_6$-alkyl-OH, —CO—H, —CO—NH$_2$, —CO—NH—R$_7$, —CO—NH—OR$_7$, —SO$_2$-aryl, —SO$_2$-heteroaryl, heteroaryl, —CO—OR$_7$ or a group represented by In a second aspect, the invention comprises a composition comprising a compound of any one of Embodiments 1, 2, 3, 4, 5, 6, 3a-3b and 5a-5i and a pharmaceutically acceptable carrier, excipient, or diluent.

In a third aspect, the invention provides a method of inhibiting HCV in a cell, comprising contacting a cell in which inhibition of HCV is desired with an inhibitor of HCV according to any one of Embodiments 1-6, 3a-3b and 5a-5i or a composition according to the second aspect of the invention. Because compounds of the invention inhibit HCV, they are also useful research tools for in vitro study HCV infections in cells and cellular systems.

In a preferred embodiment of the third aspect, the invention comprises a method of treating an HCV infection in a mammal, preferably a human, comprising administering to the mammal a therapeutically effective amount of a composition according to the second aspect of the invention.

Definitions

Unless expressly stated to the contrary, the following definitions apply uniformly throughout. For simplicity, the substituents have been defined primarily as univalent chemical moieties (e.g., alkyl, aryl, etc.). Nevertheless, such terms are also used to convey corresponding multivalent moieties under the appropriate structural circumstances. All atoms are understood to have their normal number of valences for bond formation (i.e., 4 for carbon, 3 for N, 2 for O, and 2, 4, or 6 for S, depending on the oxidation state of the S). Also, where a chemical structure exists in multiple tautomeric forms, all are envisioned as part of the invention.

The term hydrocarbyl refers to a saturated, mono- or polyunsaturated straight, branched or cyclic hydrocarbon and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, acetylenyl, propynyl, cyclopropyl, and —C≡C—CH$_2$(alkyl) (including —C≡C—CH$_2$(CH$_3$). A hydrocarbyl moiety may be defined to include a "$C_0$-$C_n$-hydrocarbyl," "$C_0$-$C_n$-alkyl," or the like, in which n is an integer, as in "aryl-$C_0$-$C_3$-alkyl." In these instances a "$C_0$" moiety represents a direct bond. So, for example, "aryl-$C_0$-$C_3$-alkyl" encompasses both aryl-$C_1$-$C_6$-alkyl moieties as well as aryl moieties ($C_0$-alkyl).

An "aryl" group is a $C_5$-$C_{16}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_6$-$C_{10}$) aryl-($C_1$-$C_6$)alkyl, including, without limitation, benzyl, phenethyl, and naphthylmethyl.

The term heteroatom means O, S, —S(O)$_{0-2}$—, or N. Compounds that contain heteroatoms, such as —S(O)$_{0-2}$—, also comprise the chiral forms. Thus, the compounds according Formulae I, II, III, and IV that contain —S(O)$_{0-2}$— are meant to also comprise the chiral isomers. Further, the compounds according Formulae I, II, III, and IV comprise all types of stereochemistry, for example, racemates, enantiomers and diastereomers of the compounds. The invention also includes the various regioisomers and hydro-isomers. For example, when a bond is denoted as "——", it includes "──" or "··········"

(that is, both S and R configurations). Further, when a compound includes one or more chiral centers, each chiral center may assume any configuration independently of the others.

A "heterocyclyl" group is a mono-, bi-, or tri-cyclic structure having from 3 to 16 atoms, wherein one or more annular atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds having adjacent annular O and/or S atoms.

A particularly preferred heterocyclyl is a heteroaryl. As used herein, the term "heteroaryl" refers to groups having 5 to 16 ring atoms, preferably 5, 6, 9, or 10 ring atoms; having 6, 10, or 14 π electrons shared in a cyclic array; and having, in addition to carbon atoms, from zero to three heteroatoms per ring selected from the group consisting of N, O, and S, provided there is at least one heteroatom. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, 10, 13 or 14 ring atoms. Specifically excluded from the scope of this term are compounds having adjacent annular O and/or S atoms.

Preferred heterocyclyls and heteroaryls include, but are not limited to, acridinyl, azocinyl, benzimidazolyl, benzofuranyl, benzothiofuranyl, benzothienyl, benzoxazolyl, benzthiazolyl, benztriazolyl, benztetrazolyl, benz-1H-tetrazolyl, benz-2H-tetrazolyl, benz-3H-tetrazolyl, benz-4H-tetrazolyl, benz-5H-tetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, benzodiazepinyl, and xanthenyl.

The term "prodrug group" is a group that forms a moiety that is converted in vivo into the active compound of Formulae I and II. Such groups are generally known in the art and include, but are not limited to, esters, alkyls, amides (—C(O)—NH—), ethers, and carbamates (—C(O$_2$)—NH—). Thus, prodrug groups include such groups that form, for example, amide, ether, or ester bonds or any other bond that can be hydrolyzed in vivo, for example, —C(O)—NH—O—. Prodrug groups comprises any leaving groups or hydrolyzable groups that when cleaved in vivo produce the corresponding active compounds of Formulae I and II.

Open valences on the radical moieties described herein can occur on any one (or more for divalent radicals) of the atoms within the moiety. For example, the $C_3$ alkyl moiety includes both propyl and isopropyl. As another example, a divalent $C_4$ alkylene moiety includes both tetramethylene (—CH$_2$(CH$_2$)$_2$CH$_2$—) and ethylethylene (—CH(CH$_2$CH$_3$)CH$_2$—).

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethyl-octyl and 3-cyclopentyl-octyl. As another example, an oxo-substituted moiety is one in which both hydrogens of a methylene (—CH$_2$—) are replaced with an oxygen to form a carbonyl (—CO—).

Substituents can be protected or unprotected as necessary, as known to those skilled in the art or as taught, for example, in Greene, et al., "Protective Groups in Organic Synthesis," John Wiley and Sons, Third Edition, 1999.

As used herein, the term pharmaceutically acceptable salt(s) refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. In another preferred embodiment, the invention comprises the compounds can also be administered as pharmaceutically acceptable quaternary salts known by those skilled in the art, which specifically include the quaternary ammonium salt of the formula —NR+Z-, wherein R is hydrogen, alkyl, or benzyl, and Z is a counter-ion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). For the purposes of the specification and claims, the term salt is intended to encompass complexes as well.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ atkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{14}$ heteroaryl or any of these rings fused or spiro-fused to a cycloalkyl, heterocyclyl, or aryl, wherein each of the foregoing is further optionally substituted with one more moieties listed in (a), above; and (c) —(CH$_2$), —NR$^{30}$R$^{31}$, wherein s is from 0 (in which case the nitrogen is directly bonded to the moiety that is substituted) to 6, and R$^{30}$ and R$^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or R$^{30}$ and R$^{31}$ taken together with the N to which they are be attached form a heterocyclyl or heteroaryl, each of which is optionally substituted with from 1 to 3 substituents from (a), above.

The term "halogen" or "halo" as employed herein refers to chlorine, bromine, fluorine, or iodine. When the term "halo" is used to describe a moiety, as in, for example, —O-halo($C_1$-$C_6$-alkyl) or halo($C_1$-$C_6$-alkyl), the moiety comprises mono- to per-halogenated groups. For example, —O-halo($C_1$-$C_6$-alkyl) comprises such groups as monohaloalkoxy, dihaloalkoxy, trihaloalkoxy, etc. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., NH$_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include NH$_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluoro-3-propylphenyl. As another non-limiting example, substituted n-octyls include 2,4 dimethyl-5-ethyl-octyl and 3-cyclopentyl-octyl. Included within this definition are methylenes (—CH$_2$—) substituted with oxygen to form carbonyl (—CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Preferred embodiments of a particular genus of compounds of the invention include combinations of preferred embodiments.

As used herein, the term pharmaceutically acceptable salt(s) refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula NR$_7^+$Z$^-$, wherein R$_7$ is hydrogen, alkyl, or benzyl, and Z is a counter-ion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The compounds of Tables 1 to 5 are named based on the numbering system provided by ChemDraw Ultra Version 9.0.1 and by ACD Labs Version 6.0. Specifically, the numbering systems used for naming the compounds of Tables 1 to 5 are based on Structures 1 and 2 shown below.

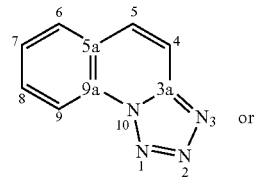

Structure 1

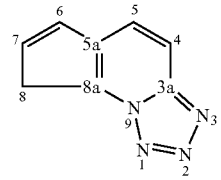

Structure 2

The active compound is included in the pharmaceutically acceptable carrier or diluent in an amount sufficient to deliver to a patient a therapeutically effective amount without causing serious toxic effects in the patient treated. The term "therapeutically effective amount" is meant to denote a dosage sufficient to inhibit proliferation of the virus in the patient. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. An oral dosage of 1-500, preferably 10-250, more preferably 25-250 mg is usually suitable.

The active ingredient should be administered to achieve peak plasma concentrations of the active compound of about 0.001-30 µM, preferably about 0.01-10 µM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/ or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. See generally "Remington's Pharmaceutical Sciences," Mack Publishing Co., Easton, Pa.

The active compound or pharmaceutically acceptable salt thereof can be administered as a component of an elixir, suspension, syrup, wafer, chewing gum or the like. Syrup may contain, in addition to the active compounds, sucrose as a sweetening agent and certain preservatives, dyes and colorings and flavors.

The active compound and pharmaceutically acceptable salts, hydrates, solvates and N-oxides thereof can also be mixed with other active materials that do not impair the desired action, or with materials that supplement the desired action, such as antibiotics, antifungals, other anti-inflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation (CA) and Gilford Pharmaceuticals (Baltimore, Md.). Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidylcholine, arachadoyl phosphatidylcholine, and cholesterol) in an inorganic solvent that is then evaporated, leaving behind a thin film of dried lipid on the surface of the container. Aqueous solutions of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Synthesis

The compounds of the invention can be synthesized according to the scheme presented below using methods well known to those skilled in the art. The synthesis procedures described in the schemes below, as well as methods well known to those skilled in the art are practised using safety precautions known in the art for azide and tetrazole chemistries. One skilled in the art will recognize that the substituents of the starting compound 1 can be varied using well known synthetic procedures. For example, various types of substitution reactions can take place on the phenyl group of compound 1 to give the alkoxy, alkyl, haloalkyl, or sulfonylalkyl product. Similarly, various types of substitution reactions or condensation reactions on any of the species in Scheme 1 will result in the various compounds described in this invention. For example, compound 5 can be reacted with any suitable amine instead of H$_2$N-OTHP. Also, one of ordinary skill in the art would recognize that analogous chemistry can be done on heteroaryl analogs of compound 1, so long as the analogous "aniline nitrogen" in the starting compound has an adjacent CH for ring annulation as outlined below. Examples of such starting materials would include, but not be limited to, the following optionally substituted heteroaryls:

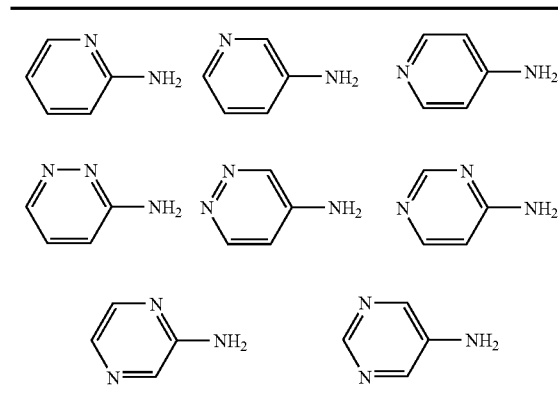

EXAMPLE 1

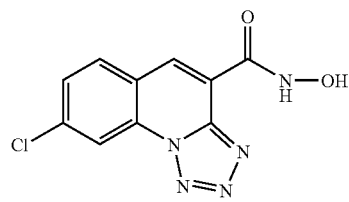

8-chloro-N-hydroxytetrazolo[1,5-a]quinoline-4-carboxamide (7)

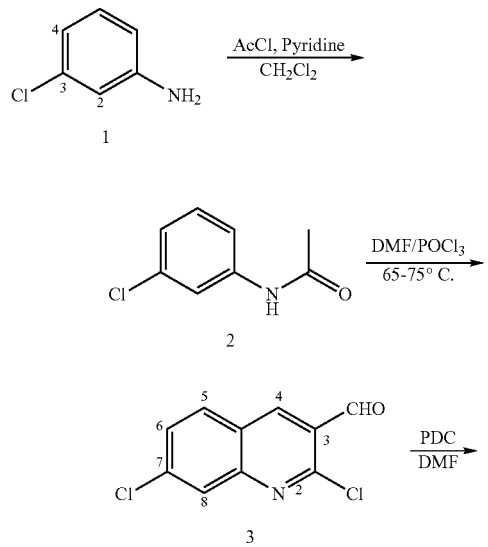

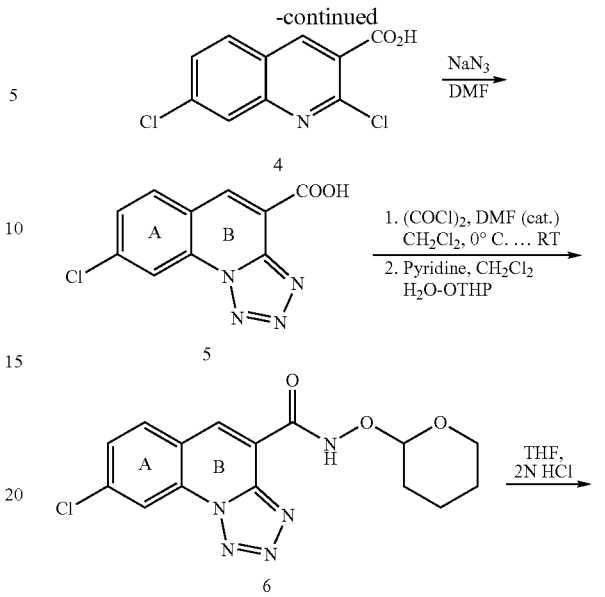

2,7-Dichloro-3-formylquinoline (3): To a dry reaction flask equipped with a reflux condenser, a magnetic stirring bar and a rubber septum with a $N_2$ inlet was placed 3-chloroacetanilide (2) (8.45 g, 50 mmol) and $POCl_3$ (34 mL, 365 mmol). The reaction mixture was cooled to 0° C. and to it was added DMF (10.5 mL, 135 mmol) over a period of 20 minutes. It was stirred at that temperature for 1 h and then at 65-75° C. for 24 h. The resulting slurry was cooled to room temperature, poured over a crushed-ice (1 Kg), digested for 1 h, the resulting solid was filtered, washed well with water and dried to give 5.26 g (47%) of the desired 2,7-dichloro-3-formylquinoline 3. $^1$H NMR ($CDCl_3$): δ 10.54 (s, 1H), 8.74 (s, 1H), 8.07 (d, 1H, J=2.1 Hz), 7.93 (d, 1H, J=9.0 Hz), 7.61 (dd, 1H, J=2.4 and 8.7 Hz); LCMS: 30.83 min.; MS (m/z): 226 (M$^+$).

2,7-Dichloroquinoline-3-carboxylic Acid (4): A dry reaction flask equipped with a magnetic stirring bar and a rubber septum was charged with 2,7-dichloro-3-formylquinoline 3 (1.1 g, 5 mmol), PDC (3.76 g, 10 mmol) and dry DMF (5 mL) and stirred at room temperature for 24 h. The reaction mixture was diluted with water (500 mL), filtered, the filtrate was saturated with NaCl and the resulting aqueous solution was extracted with EtOAc (3×200 mL). The EtOAc extract was dried over anhydrous $Na_2SO_4$ and solvent was removed to give 1.02 g (85%) of the desired 2,7-dichloroquinoline-3-carboxylic acid 4. TLC Rf: 0.12 (20% MeOH/EtOAc); $^1$H NMR (acetone $d_6$): 8.96 (s, 1H); 8.22 (d, 1H, J=9.0 Hz), 8.04 (d, 1H, J=1.8 Hz), 7.97 (bs, 1H), 7.74 (dd, 1H, J=1.8 and 8.7 Hz); LCMS (ret. time): 25.15 min.; MS (m/z): 241 (MH$^+$).

8-Chlorotetrazolo[1,5-a]quinoline-4-carboxylic Acid (5): To a dry reaction vial with a screw cap was placed 2,7-dichloroquinoline-3-carboxylic acid (0.241 g, 1 mmol), sodium azide (0.078 g, 1.2 mmol) and dry DMF (3 mL) and shaken at 65-75° C. for a period of 24 h. The reaction mixture was diluted with water (100 mL), saturated with NaCl, the resulting solid was filtered and dried to give 0.100 g (41%) of the carboxytetrazole 5. TLC Rf: 0.06 (20% MeOH/EtOAc); $^1$H NMR (DMSO d$_6$+CDCl$_3$): δ 8.71 (bs, 1H), 8.60 (s, 1H), 8.30 (d, 1H, J=7.8 Hz), 7.79 (d, 1H, J=7.5 Hz); LCMS (ret. time): 21.28; MS (m/z): 249 (MH$^+$).

8-chloro-N-(tetrahydro-2H-pyran-2-yloxy) tetrazolo[1,5-a]quinoline-4-carboxamide (6): To a suspension of carboxytetrazole (5, 0.05 g, 0.2 mmol) in CH$_2$Cl$_2$ (5 mL) at 0° C. under N$_2$ was added DMF (4-drops) followed by (COCl)$_2$ (IM CH$_2$Cl$_2$, 0.15 mL, 0.3 mmol) and the reaction was stirred for 1 h. The reaction solvent was removed and the resulting residue of acid chloride was dried under high vacuum. The acid chloride was then suspended in CH$_2$Cl$_2$ (5 mL), cooled to 0° C., to it was added pyridine (0.033 mL, 0.4 mmol) followed by H$_2$N-OTHP (0.035 g, 0.3 mmol), and stirred at room temperature for 24 h. The CH$_2$Cl$_2$ solution was washed with water, dried and solvent was evaporated. The resulting residue was filtered through a pad of silica gel to obtain the requisite oxamic acid ester 6. $^1$H NMR (CDCl$_3$): δ 11.58 (s, 1H), 8.92 (s, 1H), 8.74 (d, 1H, J=1.8 Hz), 8.10 (d, 1H, J=8.1 Hz), 7.77 (dd, 1H, J=1.8 Hz and 8.7 Hz), 5.26 (m, 1H), 4.15 (m, 1H), 3.76 (m, 1H), 2.10-1.50 (m, 6H); LCMS (ret. time): 21.46 min.; MS (m/z): 347 (MH$^+$).

8-chloro-N-hydroxytetrazolo[1,5-a]quinoline-4-carboxamide (7): To a solution of THP oxamate 6 (0.035 g, 0.1 mmol) in THF (1 mL) was added 2N HCl (1 mL) and stirred at room temperature for 6 h. The reaction solvent was removed under a reduced pressure and the resulting aqueous solution was diluted with water. The precipitated solid was filtered, washed with water and dried to give the desired oxamic acid 7. $^1$H NMR (CDCl$_3$): δ 8.80 (s, 1H), 8.64 (bd, 1H), 8.06 (d, 1H, J=8.1 Hz), 7.70 (dd, 1H, J=2.4 and 8.7 Hz), LCMS (ret. time): 20.47 min.; MS (m/z): 264 (MH$^+$).

EXAMPLE 2

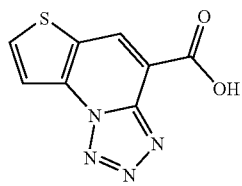

tetrazolo[1,5-a]thieno[2,3-e]pyridine-4-carboxylic acid (12)

EXAMPLE 2a

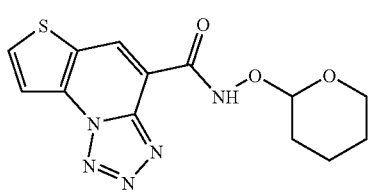

N-(tetrahydro-2H-pyran-2-yloxy)tetrazolo[1,5-a]thieno[2,3-e]pyridine-4-carboxamide (13)

EXAMPLE 2b

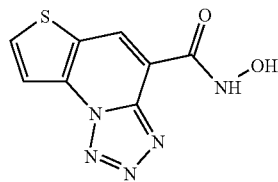

N-hydroxytetrazolo[1,5-a]thieno[2,3-e]pyridine-4-carboxamide (14)

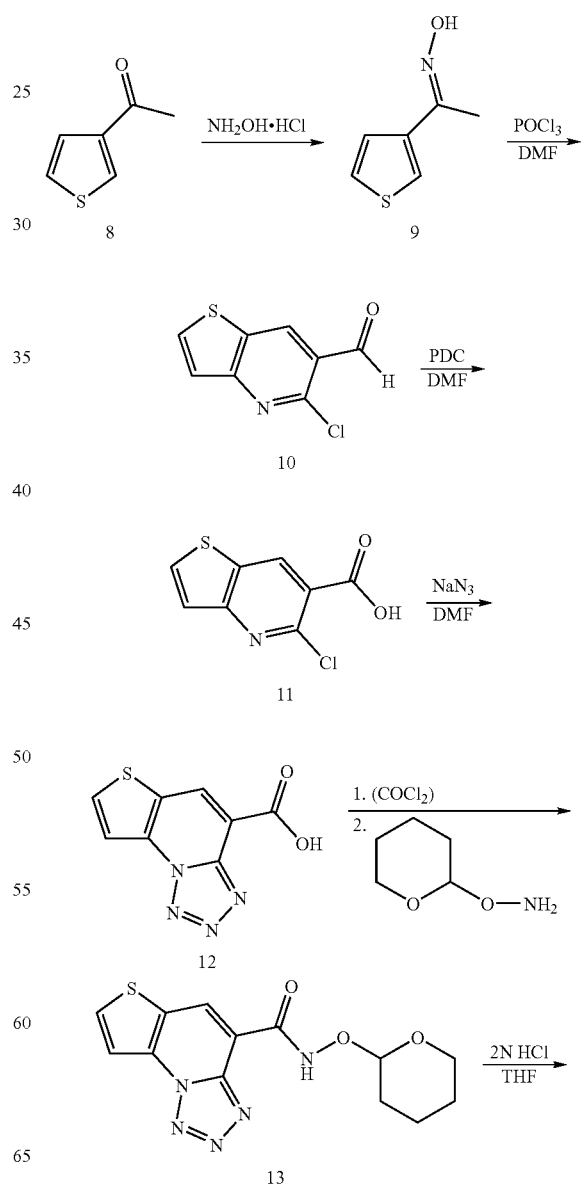

Scheme II

-continued

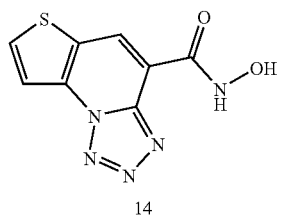

14

Preparation of E & Z of 3-acetylthiopheneoxime (9): To a solution of hydroxylamine hydrochloride (6.66 g, 0.096 mole) in water (15 mL) was added 20% NaOH solution (20 mL). The mixture was cooled in an ice-bath and 3-acetylthiophene (10 g, 0.08 mole) was added. The reaction mixture was allowed to warm to room temperature and then heated at 100° C. for over-night. Upon cooling, solid separated which was collected by filtration. Recrystallized from hot water gave colorless solid 9.38 g (83%) of desired product 9. $^1$H NMR (CDCl$_3$, 300 MHz): δ 8.65 (s, 1H), 7.46 (d, 1H, J=1.5 Hz), 7.40 (d, 1H, J=1.2 Hz), 7.31 (d, 1H, J=3.0 Hz), 2.28 (s, 3H); LCMS (m/z): 142 (MH$^+$).

Preparation of 5-chlorothienyl[3,2-b]pridine-6-carboxaldehyde (10): To a solution of oxime 9 (4.0 g, 28.37 mmol) in ether (40 mL), cooled in an ice/water bath was slowly added POCl$_3$ (25.6 mL). The temperature of the reaction mixture was maintained at 0-100C for 2 h while DMF (4.88 mL) was slowly added. The temperature of the reaction was raised and the ether was distilled off. The temperature was increased to 110 IC for over-night. Using this procedure, the Vilsmeier reagent, Me$_2$N$^+$=CHCl Cl$^-$, is generated in situ. The reaction was then cooled in an ice/water bath, quenched by adding ice and finally water (100 mL). The contents were cooled in an ice-water bath, then filtered and dried well to give 1.37 g (24%) desired product. $^1$H NMR (CDCl$_3$, 300 MHz): δ 10.51 (d, 1H), 8.73 (d, 1H, J=0.6 Hz), 8.07 (d, 1H, J=5.7 Hz), 7.57 (dd, 1H, J=0.6 and 5.4 Hz); LCMS (m/z): 197 (MH$^+$).

Compounds 11-14 were prepared by using above representative procedures of compounds 4-7.

Analogously, the following compounds were made using above representative prodecures:

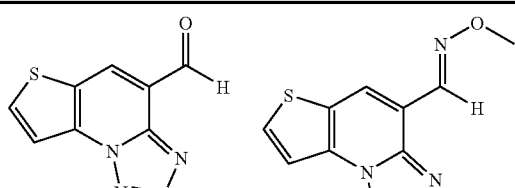

tetrazolo[1,5-a]thieno[2,3-e]pyridine-4-carbaldehyde tetrazolo[1,5-a]thieno[2,3-e]pyridine-4-carbaldehyde O-methyloxime One of ordinary skill in the art would recognize that analogous chemistry can be done on heteroaryls analogous to compound 8, so long as the keto-functionality has an adjacent CH for ring annulation as outlined above. Examples of such starting materials would include, but not be limited to, the following optionally substituted heteroaryls:

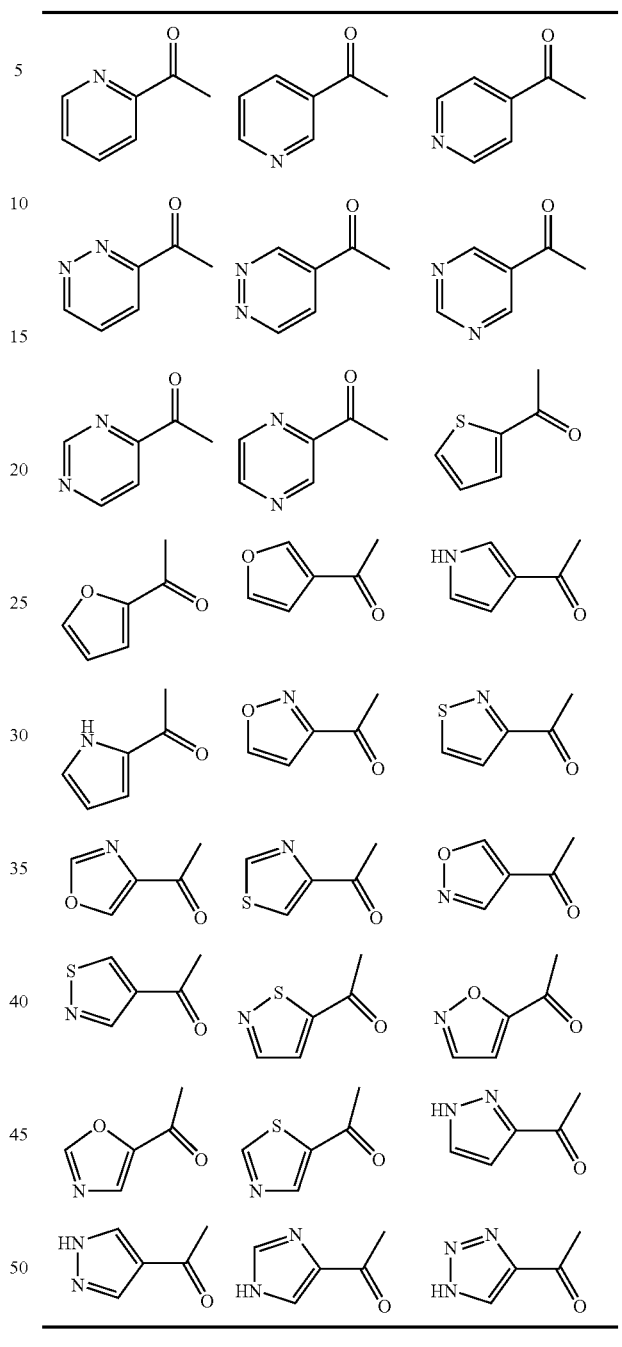

EXAMPLE 3

The compounds of the invention according to formula V can be synthesized according to the scheme III presented below using methods well known to those skilled in the art. One of ordinary skill in the art would recognize that analogous chemistry can be done on other fused heteroaryls analogous to compound 1a (below), so long as the nitrile-functionality can be installed on the "A" ring as outlined in Scheme III. As well, 2-halo (or other leaving group-containing) pyridines are commercially available and analogous heterocycles can be synthesized as outlined in Scheme II above using as starting materials, for example those listed above that are analogous to compound 8. For convenience, compounds 3a, 4a, 5a 6a and 7a are depicted as the corresponding 3H-tetrazole. One of ordinary skill in the art would recognize that, depending on reaction conditions, mixtures of the 1H-tetrazole and the 3H-tetrazole are possible along with, less commonly, the 5H-tetrazole isomer.

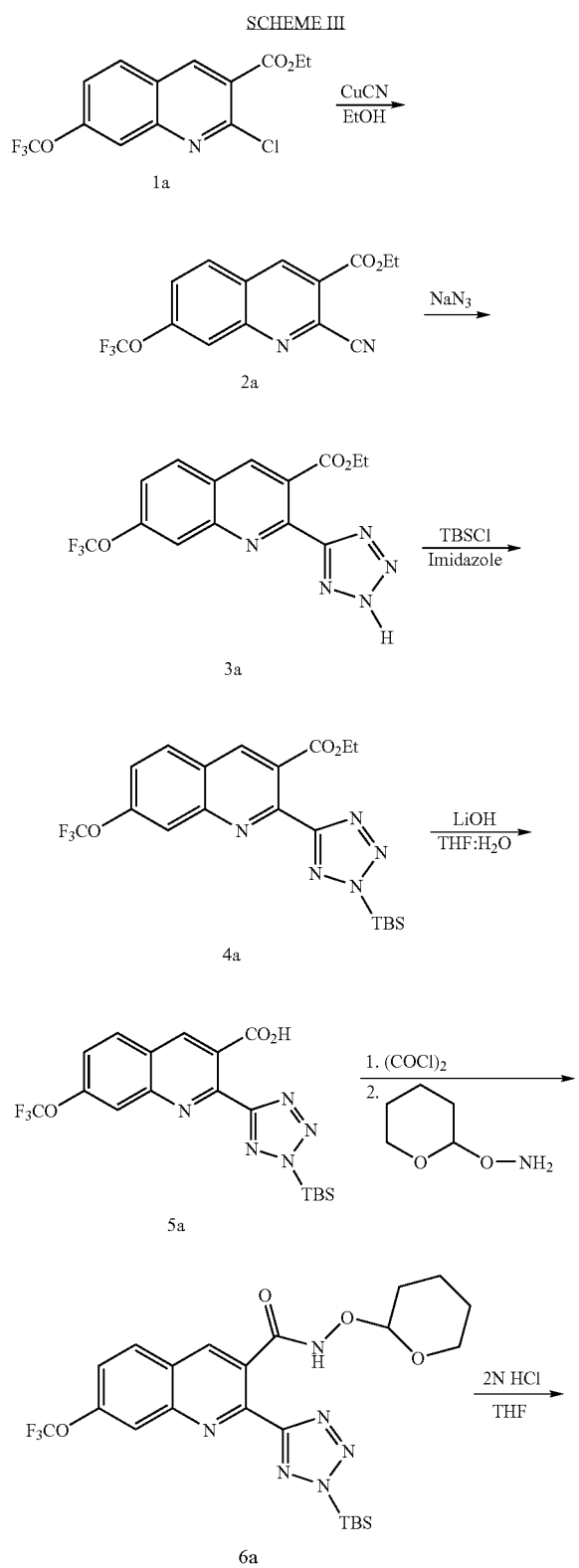

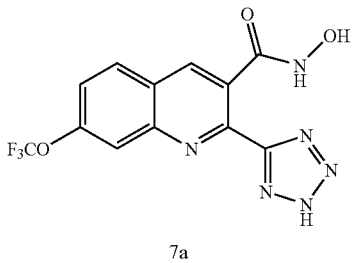

7a

Biological Assay

The following assay examples illustrate the HCV inhibitory properties of the compounds of the invention.

ASSAY EXAMPLE 1

HCV Replicon Assay

Actively dividing 5-2Luc replicon cells were seeded at the density of 5000-7500 cells/well in the volume of 90 µl/well into 96 well plate(s). The cells were then incubated at 37° C. and 5% $CO_2$ for 24 hours. The 5-2 cells are replicon cells licensed from Ralf Bartenschlager (Germany) and have a self-replicating RNA molecule in the Huh7 cell; the RNA contains HCV non-structural proteins that make the self-replication possible.

Various concentrations of compounds (in the volume of 10 µl) were added into each well 24 hours after seeding the cells. The cells were incubated for another 24 hours before luciferase assay.

After incubating the 5-2Luc replicon cells with the compounds for 24 hours, media were aspirated from each well and Bright-Glo (Pharmacia) luciferase assay reagents were added to each well according to the manufacturer's manual. Briefly, the Bright-Glo reagent was diluted with equal volume of PBS and an aliquote (100 µl) was added to each well. After incubating the plate at room temperature for 5 minutes, luciferase counts were taken using a luminometer.

ASSAY EXAMPLE 2

Luciferase Counter Assay

Actively dividing CMV-Luc cells (Luc cells in which DNA construct (CMV promoter followed by Luciferase gene) is permanently integrated into the chromosome of Huh7 cells) were seeded at the density of 5000-7500 cells/well in the volume of 90 µl/well into 96 well plate(s). The cells were then incubated at 37° C. and 5% $CO_2$ for 24 hours.

Various concentrations of compounds (in the volume of 10 µl) were added into each well 24 hours after seeding the cells. The cells were incubated with the compounds for another 24 hours before luciferase assay.

After incubating the CMV-Luc cells with the compounds for 24 hours, media were aspirated from each well and Bright-Glo (Pharmacia) luciferase assay reagents were added to each well according to the manufacturer's manual. Luciferase counts were taken using a luminometer.

The activity of a number of compounds according to the invention measured by the luciferase assay is displayed in Table 1.

ASSAY EXAMPLE 3

Immunoblotting Assay

Actively dividing 9-13 replicon cells (Huh7 cells comprising an HCV replicon) were seeded at the density of $1\times10^5$ cells/well in the volume of 2 ml/well into 6 well plate(s). The cells were then incubated at 37° C. and 5% $CO_2$ for 24 hours.

Various concentrations of compounds (in the volume of 10 μl) were added into each well 24 hours after seeding the cells. The cells were incubated with the compounds for another 48 hours.

Protein samples were prepared from the cultured cells and resolved on a SDS-PAGE gel.

After electrophoresis, the protein samples on the SDS-PAGE gel were transferred to a nitrocellulose membrane.

The membrane was blocked with 5% non-fat milk in PBS for 1 hr at room temperature.

Primary antibody incubation was performed for 1 hour at room temperature before the membrane was washed for 3 times with PBST (PBS plus 0.1% Tween 20), 15 minutes each.

Horse Radish Peroxidase conjugated secondary antibody incubation was performed for 1 hour at room temperature before the membrane was washed for 3 times with PBST (PBS plus 0.1% Tween 20), 15 minutes each.

The membrane was then soaked in substrate solution (Pierce) and exposed to a film.

ASSAY EXAMPLE 4

TaqMan RT-PCR Assay

Actively dividing 9-13 replicon cells were seeded at the density of $3\times10^4$ cells/well in the volume of 1 ml/well into 24 well plate(s). The cells were then incubated at 37° C. and 5% $CO_2$ for 24 hours.

Various concentrations of compounds (in the volume of 10 μl) were added into each well 24 hours after seeding the cells. The cells were incubated with the compounds for another 24 hours.

After incubating the 9-13 replicon cells with the compounds for 24 hours, media were aspirated off and RNA samples were prepared from each well.

TaqMan® (Roche Molecular Systems) one step RT-PCR was performed using the RNA samples according to the manufacturer's manual. Briefly, properly diluted RNA sample, upstream primer, downstream primer, FAM-labeled probe oligo were mixed and water was added to make up the volume to 25 μl. Equal volume of 2× TaqMan Master Mix were added and the reaction was performed in an ABI Prism 7700 Sequence Detector (Applied Biosystems).

The compounds in Table 1 to 3 immediately below were prepared essentially using the methods described herein and illustrated in the schemes. All of the compounds in this application were named using Chemdraw Ultra version 6.0.2, which is available through Cambridgesoft.co, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

The compounds of Table 1 below exhibited greater than 20% inhibitory activity.

TABLE 1

| Structure | Name |
|---|---|
| 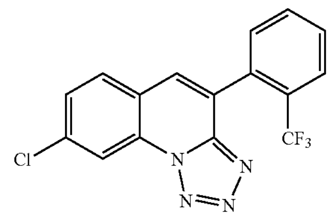 | 8-chloro-4-[2'-(trifluoromethyl)-phenyl]tetrazolo-[1,5-a]quinoline |
| 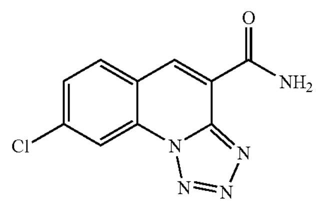 | 8-chlorotetrazolo-[1,5-a]quinoline-4-carboxamide |
| 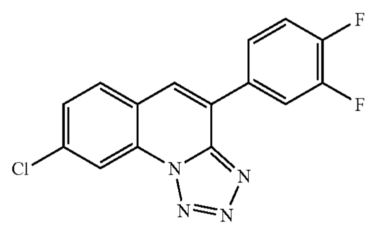 | 8-chloro-4-(3',4'-difluorophenyl)-tetrazolo[1,5-a]quinoline |
| 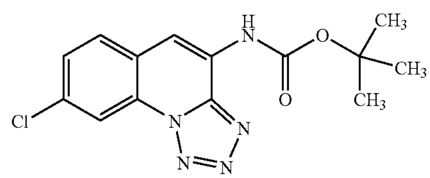 | tert-butyl (8-chlorotetrazolo-[1,5-a]quinolin-4-yl)carbamate |
| | 9-(trifluoromethyl)tetrazolo-[1,5-a]quinoline-4-carboxylic acid |
| 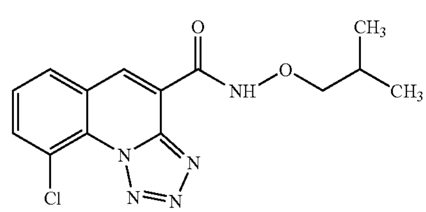 | 9-chloro-N-isobutoxy-tetrazolo[1,5-a]quinoline-4-carboxamide |
| 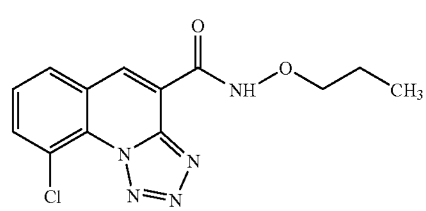 | 9-chloro-N-n-propoxytetrazolo-[1,5-a]quinoline-4-carboxamide |

TABLE 1-continued

| Structure | Name |
|---|---|
| 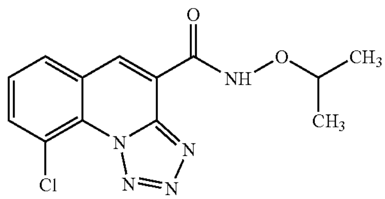 | 9-chloro-N-isopropoxy-tetrazolo[1,5-a]quinoline-4-carboxamide |
| 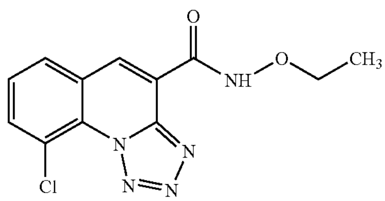 | 9-chloro-N-ethoxytetrazolo-[1,5-a]quinoline-4-carboxamide |
| 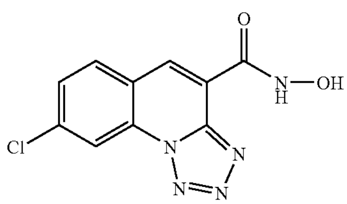 | 8-chloro-N-hydroxytetrazolo-[1,5-a]quinoline-4-carboxamide |

The compounds of Table 2 exhibited 5% to 20% inhibitory activity.

TABLE 2

| Structure | Name |
|---|---|
| 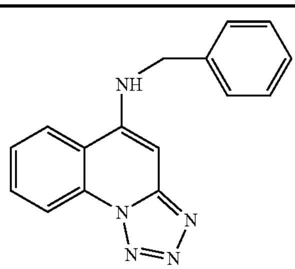 | N-benzyltetrazolo[1,5-a]quinolin-5-amine |
| 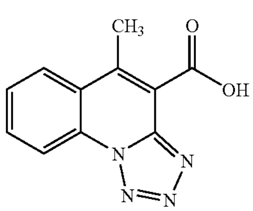 | 5-methyltetrazolo[1,5-a]quinoline-4-carboxylic acid |
| 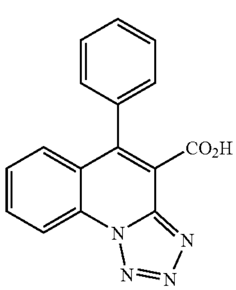 | 5-phenyltetrazolo[1,5-a]quinoline-4-carboxylic acid |

TABLE 2-continued

| Structure | Name |
|---|---|
| 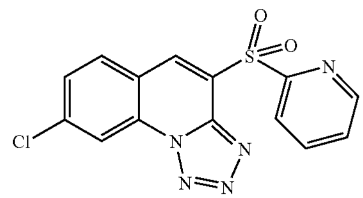 | 8-chloro-4-(pyridin-2'-yl-sulfonyl)tetrazolo-[1,5-a]quinoline |
| 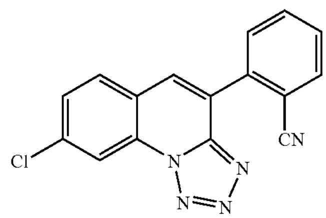 | 2-(8-chlorotetrazolo[1,5-a]quinolin-4-yl)benzonitrile |
| 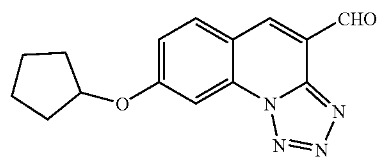 | 8-(cyclopentyloxy)-tetrazolo[1,5-a]quinoline-4-carbaldehyde |
| 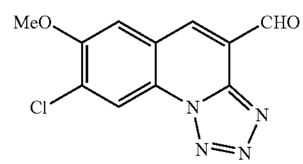 | 8-chloro-7-methoxytetrazolo-[1,5-a]quinoline-4-carbaldehyde |
| 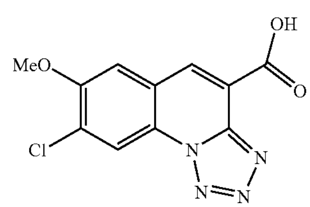 | 8-chloro-7-methoxytetrazolo-[1,5-a]quinoline-4-carboxylic acid |
| 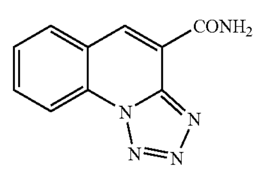 | tetrazolo[1,5-a]quinoline-4-carboxamide |
| 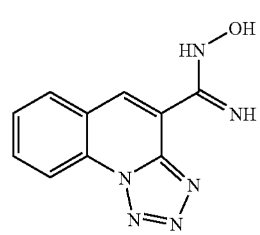 | N-hydroxytetrazolo-[1,5-a]quinoline-4-carboximidamide |
| 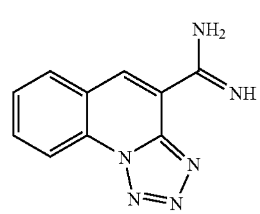 | tetrazolo[1,5-a]quinoline-4-carboximidamide |

TABLE 2-continued

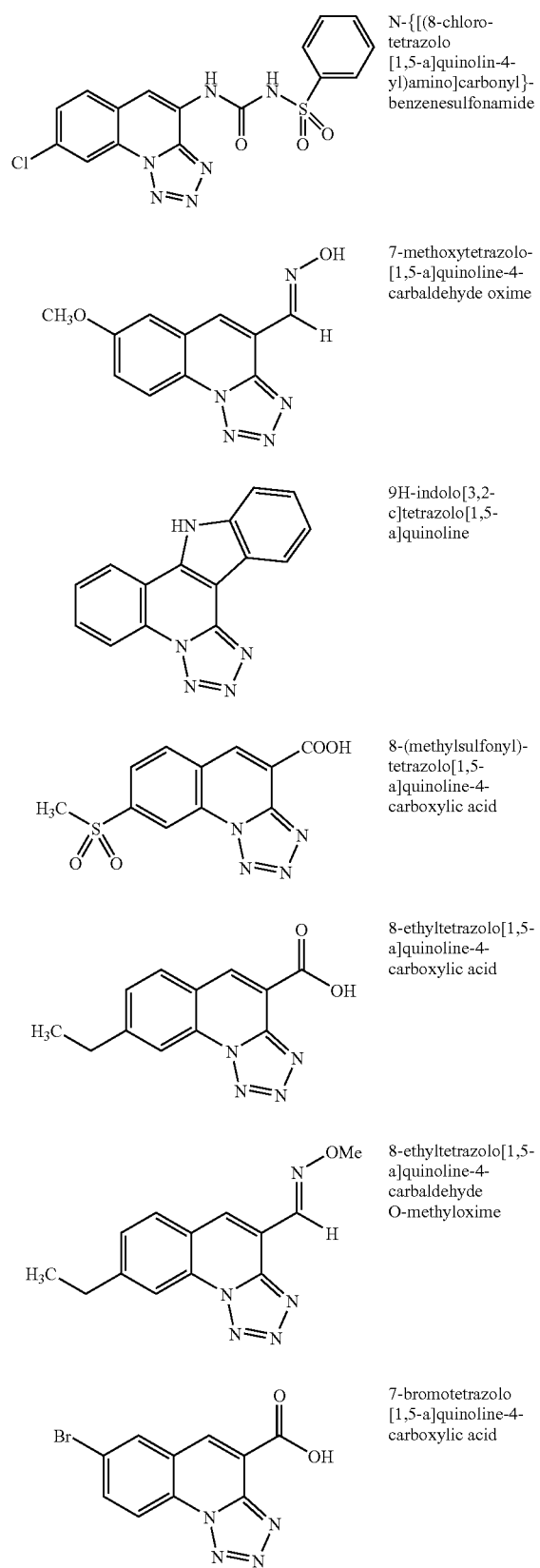

| Structure | Name |
|---|---|
| (8-chloro, phenylsulfonyl urea) | N-{[(8-chloro-tetrazolo[1,5-a]quinolin-4-yl)amino]carbonyl}-benzenesulfonamide |
| (7-methoxy, CH=NOH) | 7-methoxytetrazolo-[1,5-a]quinoline-4-carbaldehyde oxime |
| (indolo-fused) | 9H-indolo[3,2-c]tetrazolo[1,5-a]quinoline |
| (8-methylsulfonyl, COOH) | 8-(methylsulfonyl)-tetrazolo[1,5-a]quinoline-4-carboxylic acid |
| (8-ethyl, COOH) | 8-ethyltetrazolo[1,5-a]quinoline-4-carboxylic acid |
| (8-ethyl, CH=NOMe) | 8-ethyltetrazolo[1,5-a]quinoline-4-carbaldehyde O-methyloxime |
| (7-bromo, COOH) | 7-bromotetrazolo[1,5-a]quinoline-4-carboxylic acid |

TABLE 2-continued

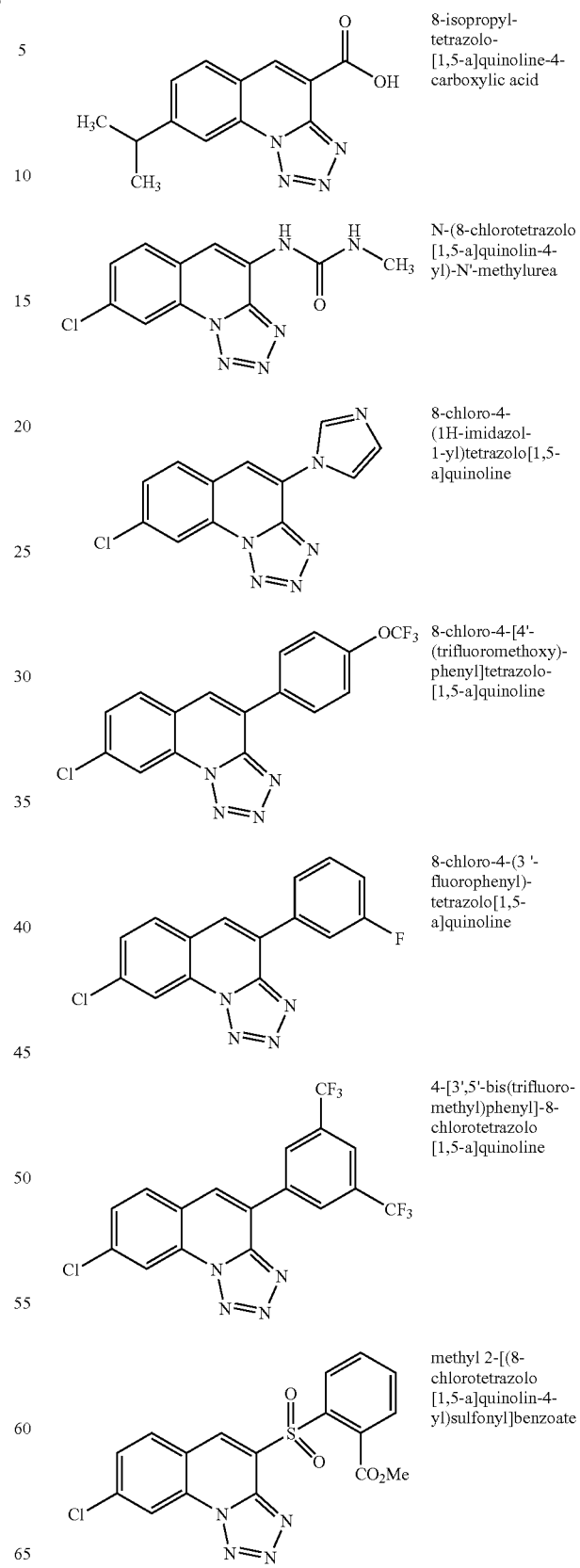

| Structure | Name |
|---|---|
| (8-isopropyl, COOH) | 8-isopropyl-tetrazolo-[1,5-a]quinoline-4-carboxylic acid |
| (8-chloro, N-methylurea) | N-(8-chlorotetrazolo[1,5-a]quinolin-4-yl)-N'-methylurea |
| (8-chloro, imidazolyl) | 8-chloro-4-(1H-imidazol-1-yl)tetrazolo[1,5-a]quinoline |
| (8-chloro, 4'-OCF3 phenyl) | 8-chloro-4-[4'-(trifluoromethoxy)-phenyl]tetrazolo-[1,5-a]quinoline |
| (8-chloro, 3'-fluorophenyl) | 8-chloro-4-(3'-fluorophenyl)-tetrazolo[1,5-a]quinoline |
| (8-chloro, 3',5'-bisCF3 phenyl) | 4-[3',5'-bis(trifluoromethyl)phenyl]-8-chlorotetrazolo[1,5-a]quinoline |
| (8-chloro, sulfonyl benzoate) | methyl 2-[(8-chlorotetrazolo[1,5-a]quinolin-4-yl)sulfonyl]benzoate |

TABLE 2-continued

| Structure | Name |
|---|---|
| (8-chloro, 3'-OCF3 phenyl substituent) | 8-chloro-4-[3'-(trifluoromethoxy)-phenyl]tetrazolo[1,5-a]quinoline |
| (7-fluoro, 8-piperidinyl, 4-CO2Et) | ethyl 7-fluoro-8-piperidin-1-yltetrazolo[1,5-a]quinoline-4-carboxylate |
| (8-MeS, 4-CHO) | 8-(methylthio)-tetrazolo[1,5-a]quinoline-4-carbaldehyde |
| (8-MeO, 4-CHO) | 8-methoxytetrazolo-[1,5-a]quinoline-4-carbaldehyde |
| (8-Cl, 4-C(O)NHCH2Ph) | N-benzyl-8-chlorotetrazolo[1,5-a]quinoline-4-carboxamide |
| (8-OCF3, 4-COOH) | 8-(trifluoromethoxy)tetrazolo-[1,5-a]quinoline-4-carboxylic acid |
| (8,9-dioxino fused, 4-COOH) | 8,9-dihydro[1,4]-dioxino[2,3-g]tetrazolo[1,5-a]quinoline-4-carboxylic acid |
| (7-Cl, 4-COOH) | 7-chlorotetrazolo[1,5-a]quinoline-4-carboxylic acid |
| (8-Cl, 4-C(O)NH-O-THP) | 8-chloro-N-(tetrahydro-2H-pyran-2-yloxy)tetrazolo[1,5-a]quinoline-4-carboxamide |
| (8-CF3, 4-CO2Na) | sodium 8-(trifluoromethyl)-tetrazolo[1,5-a]quinoline-4-carboxylate |
| (8-OCF3, 4-CO2Na) | sodium 8-(trifluoromethoxy)-tetrazolo[1,5-a]quinoline-4-carboxylate |
| (6-N3, 4-CO2Et) | ethyl 6-azidotetrazolo[1,5-a]quinoline-4-carboxylate |
| (8-NH2, 4-CO2Me) | methyl 8-aminotetrazolo[1,5-a]quinoline-4-carboxylate |
| (9-Me, 4-COOH) | 9-methyltetrazolo[1,5-a]quinoline-4-carboxylic acid |
| (9-Cl, 4-CO2-n-Bu) | n-butyl 9-chlorotetrazolo[1,5-a]quinoline-4-carboxylate |

TABLE 2-continued

| | |
|---|---|
| 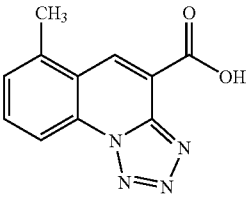 | 6-methyltetrazolo[1,5-a]quinoline-4-carboxylic acid |
| 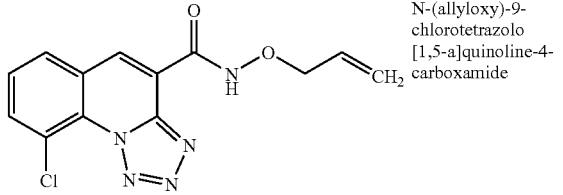 | N-(allyloxy)-9-chlorotetrazolo[1,5-a]quinoline-4-carboxamide |
| 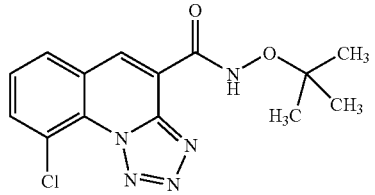 | N-(tert-butoxy)-9-chlorotetrazolo[1,5-a]quinoline-4-carboxamide |
| 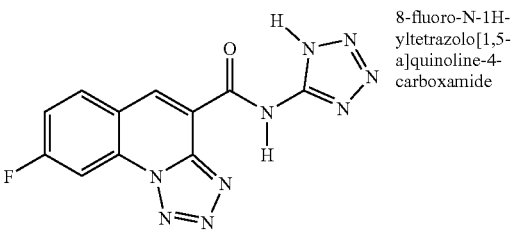 | 8-fluoro-N-1H-yltetrazolo[1,5-a]quinoline-4-carboxamide |
| 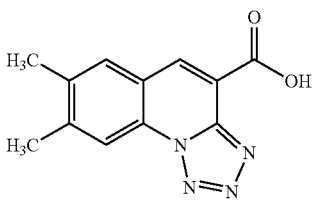 | 7,8-dimethyl-tetrazolo[1,5-a]quinoline-4-carboxylic acid |
| 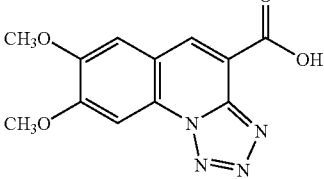 | 7,8-dimethoxy-tetrazolo[1,5-a]quinoline-4-carboxylic acid |
| 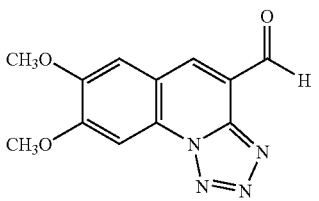 | 7,8-dimethoxy-tetrazolo[1,5-a]quinoline-4-carbaldehyde |

TABLE 2-continued

| | |
|---|---|
| 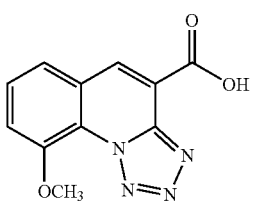 | 9-methoxy-tetrazolo[1,5-a]quinoline-4-carboxylic acid |
| 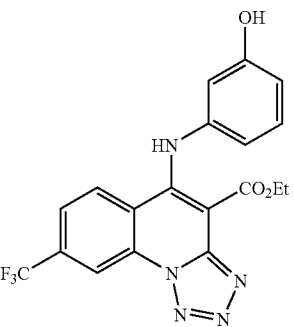 | ethyl 5-[(3'-hydroxyphenyl)-amino]-8-(trifluoromethyl)-tetrazolo[1,5-a]quinoline-4-carboxylate |

Compounds exhibiting less than 5% inhibitory activity are listed in Table 3 below.

TABLE 3

| | |
|---|---|
| 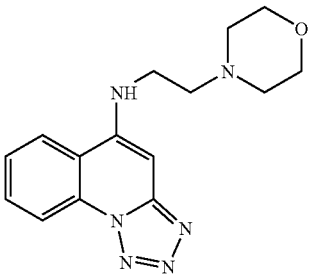 | N-(2'-morpholin-4-ylethyl)-tetrazolo[1,5-a]quinolin-5-amine |
| 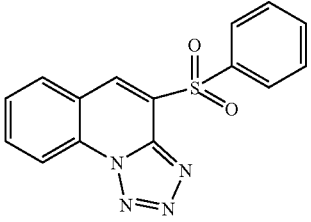 | 4-(phenyl-sulfonyl)-tetrazolo[1,5-a]quinoline |
| 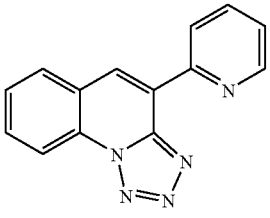 | 4-pyridin-2'-yltetrazolo-[1,5-a]quinoline |

TABLE 3-continued

| Structure | Name |
|---|---|
| (4-pyridin-3'-yl compound) | 4-pyridin-3'-yltetrazolo-[1,5-a]-quinoline |
| (tetrazolo[1,5-a]quinoline-5-carboxylic acid) | tetrazolo[1,5-a]quinoline-5-carboxylic acid |
| (4-phenyl compound) | 4-phenyl-tetrazolo[1,5-a]quinoline |
| (8-chloro-4-pyridin-4'-yl compound) | 8-chloro-4-pyridin-4'-yltetrazolo[1,5-a]quinoline |
| (8-chloro-4-[3'-(trifluoromethyl)phenyl] compound) | 8-chloro-4-[3'-(trifluoromethyl)phenyl]-tetrazolo[1,5-a]quinoline |
| (8-chloro-4-(3'-methoxyphenyl) compound) | 8-chloro-4-(3'-methoxyphenyl)-tetrazolo[1,5-a]quinoline |
| (8-chloro-4-(2'-methoxyphenyl) compound) | 8-chloro-4-(2'-methoxyphenyl)-tetrazolo[1,5-a]quinoline |
| (4-phenyl compound) | 4-phenyl-tetrazolo[1,5-a]quinoline |
| (4-(1H-imidazol-1-yl) compound) | 4-(1H-imidazol-1-yl)tetrazolo-[1,5-a]-quinoline |
| (4-(1H-1,2,4-triazol-1-yl) compound) | 4-(1H-1,2,4-triazol-1-yl)-tetrazolo[1,5-a]quinoline |
| (8-chloro-4-pyridin-3'-yl compound) | 8-chloro-4-pyridin-3'-yl-tetrazolo[1,5-a]quinoline |
| (4-(1,3-benzothiazol-2-yl)-8-chloro compound) | 4-(1,3-benzothiazol-2-yl)-8-chloro-tetrazolo[1,5-a]quinoline |
| (8-chloro-4-(2'-nitrophenyl) compound) | 8-chloro-4-(2'-nitrophenyl)tetrazolo[1,5-a]quinoline |
| (8-chloro-4-[(1-methyl-1H-imidazol-2-yl)sulfonyl] compound) | 8-chloro-4-[(1-methyl-1H-imidazol-2-yl)sulfonyl]-tetrazolo[1,5-a]quinoline |

TABLE 3-continued

| | | |
|---|---|---|
| 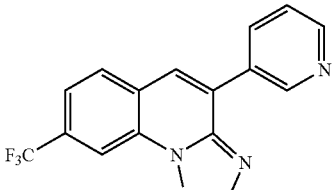 | 4-pyridin-3'-yl-8-(trifluoromethyl)-tetrazolo[1,5-a]quinoline | |
| 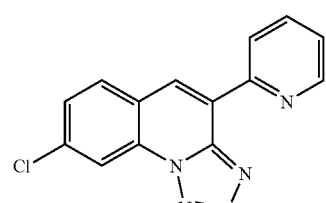 | 8-chloro-4-pyridin-2'-yltetrazolo[1,5-a]quinoline | |
| 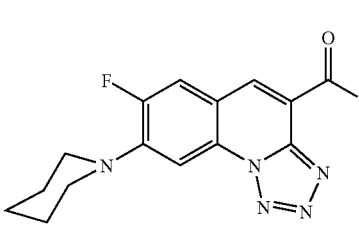 | 7-fluoro-8-piperidin-1-yltetrazolo[1,5-a]quinoline-4-carboxylic acid | |
| 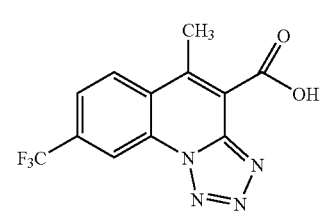 | 5-methyl-8-(trifluoromethyl)-tetrazolo[1,5-a]quinoline-4-carboxylic acid | |
| 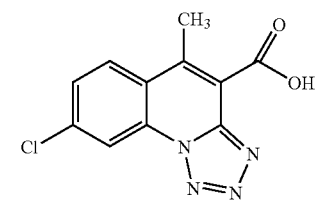 | 8-chloro-5-methyl-tetrazolo[1,5-a]quinoline-4-carboxylic acid | |
| 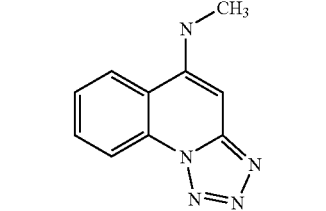 | N-methyl-tetrazolo[1,5-a]quinolin-5-amine | |
| 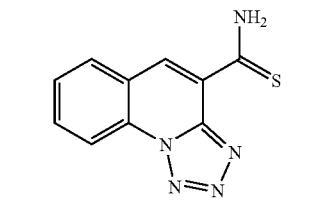 | tetrazolo[1,5-a]quinoline-carbothioamide | |

TABLE 3-continued

| | | |
|---|---|---|
| 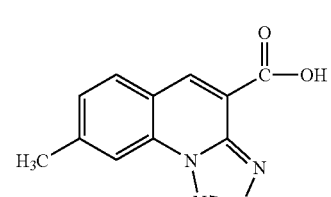 | 8-methyl-tetrazolo[1,5-a]quinoline-4-carboxylic acid | |
| 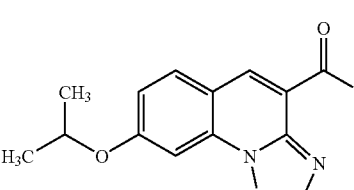 | 8-isopropoxy-tetrazolo[1,5-a]quinoline-4-carboxylic acid | |
| 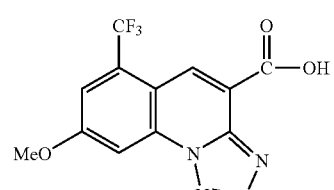 | 8-methoxy-6-(trifluoromethyl)-tetrazolo[1,5-a]quinoline-4-carboxylic acid | |
| 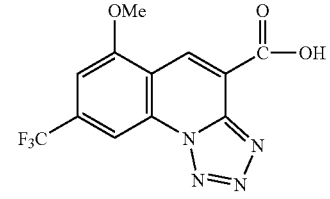 | 6-methoxy-8-(trifluoromethyl)-tetrazolo[1,5-a]quinoline-4-carboxylic acid | |
| 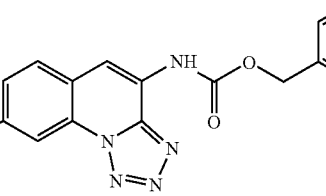 | benzyl (8-chloro-tetrazolo[1,5-a]quinolin-4-yl)carbamate | |
| 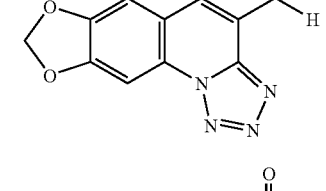 | [1,3]dioxolo[4,5-g]tetrazolo[1,5-a]quinoline 4-carbaldehyde | |
| 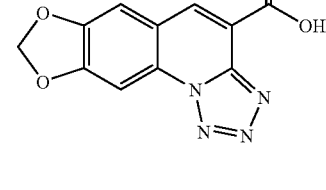 | [1,3]dioxolo[4,5-g]tetrazolo[1,5-a]quinoline-4-carboxylic acid | |

TABLE 3-continued

| Structure | Name |
|---|---|
| (structure) | 7-methyl-tetrazolo[1,5-a]quinoline-4-carboxylic acid |
| (structure) | 7-phenyl-tetrazolo[1,5-a]quinoline-carbaldehyde |
| (structure) | sodium 8-ethyl-tetrazolo[1,5-a]quinoline-4-carboxylate |
| (structure) | methyl (8-chloro-tetrazolo[1,5-a]quinolin-4-yl)carbamate |
| (structure) | ethyl (8-chloro-tetrazolo[1,5-a]quinolin-4-yl)carbamate |
| (structure) | N-n-butyl-N'-(8-chloro-tetrazolo[1,5-a]quinolin-4-yl)urea |
| (structure) | n-butyl (8-chloro-tetrazolo[1,5-a]quinolin-4-yl)carbamate |
| (structure) | tetrazolo[1,5-a]quinoline-4-carbaldehyde oxime |

TABLE 3-continued

| Structure | Name |
|---|---|
| (structure) | tetrazolo[1,5-a]quinoline-4-carbaldehyde O-methyloxime |
| (structure) | 7-methoxy-tetrazolo[1,5-a]quinoline-4-carbaldehyde O-methyloxime |
| (structure) | 8-fluoro-tetrazolo[1,5-a]quinoline-4-carboxylic acid |
| (structure) | 8-(benzyloxy)-tetrazolo[1,5-a]quinoline-4-carbaldehyde |
| (structure) | 8-(benzyloxy)-tetrazolo[1,5-a]quinoline-4-carboxylic acid |
| (structure) | 8-chloro-tetrazolo[1,5-a]quinoline-4-carboxylic acid |
| (structure) | 8-methoxy-tetrazolo[1,5-a]quinoline-4-carboxylic acid |

TABLE 3-continued

| Structure | Name |
|---|---|
| (7-fluoro tetrazolo[1,5-a]quinoline-4-carboxylic acid structure) | 7-fluoro-tetrazolo[1,5-a]quinoline-4-carboxylic acid |
| (8-chloro-N-1H-tetrazol-5-yl tetrazolo[1,5-a]quinoline-4-carboxamide structure) | 8-chloro-N-1H-tetrazol-5-yltetrazolo[1,5-a]quinoline-4-carboxamide |
| (7-fluoro-N-1H-tetrazol-5-yl tetrazolo[1,5-a]quinoline-4-carboxamide structure) | 7-fluoro-N-1H-tetrazol-5-yltetrazolo[1,5-a]quinoline-4-carboxamide |
| (8-chloro-N-[4'-(trifluoromethyl)phenyl]tetrazolo[1,5-a]quinoline carboxamide structure) | 8-chloro-N-[4'-(trifluoromethyl)-phenyl]-tetrazolo[1,5-a]quinoline carboxamide |
| (8-chloro-N,N-dimethyl-tetrazolo[1,5-a]quinoline 4-carboxamide structure) | 8-chloro-N,N-dimethyl-tetrazolo[1,5-a]quinoline 4-carboxamide |
| (8-chloro-tetrazolo[1,5-a]quinoline-4-carbaldehyde O-methyloxime structure) | 8-chloro-tetrazolo[1,5-a]quinoline-4-carbaldehyde O-methyloxime |
| (8-chloro-tetrazolo[1,5-a]quinoline 4-carbaldehyde oxime structure) | 8-chloro-tetrazolo[1,5-a]quinoline 4-carbaldehyde oxime |

TABLE 3-continued

| Structure | Name |
|---|---|
| (potassium 8-chloro-tetrazolo[1,5-a]quinoline 4-carboxylate structure) | potassium 8-chloro-tetrazolo[1,5-a]quinoline 4-carboxylate |
| (7-bromo-tetrazolo[1,5-a]quinoline-5-carboxylic acid structure) | 7-bromo-tetrazolo[1,5-a]quinoline-5-carboxylic acid |
| (8,9-dihydro-[1,4]dioxino[2,3-g]tetrazolo[1,5-a]quinoline-carbaldehyde structure) | 8,9-dihydro-[1,4]dioxino[2,3-g]tetrazolo[1,5-a]quinoline-carbaldehyde |
| (8-azido-4-(1,3-dioxolan-2-yl)tetrazolo[1,5-a]quinoline structure) | 8-azido-4-(1,3-dioxolan-2-yl)tetrazolo-[1,5-a]quinoline |
| (8-azido-tetrazolo[1,5-a]quinoline-4-carboxylic acid structure) | 8-azido-tetrazolo[1,5-a]quinoline-4-carboxylic acid |
| (ethyl 8-(trifluoromethyl)-tetrazolo[1,5-a]quinoline-4-carboxylate structure) | ethyl 8-(trifluoromethyl)-tetrazolo[1,5-a]quinoline-4-carboxylate |
| (8-(trifluoromethyl)-tetrazolo[1,5-a]quinoline-4-carboxylic acid structure) | 8-(trifluoromethyl)-tetrazolo[1,5-a]quinoline-4-carboxylic acid |

TABLE 3-continued

| | | |
|---|---|---|
| 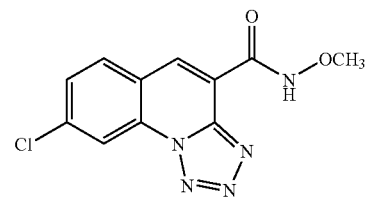 | 8-chloro-N-methoxy-tetrazolo[1,5-a]quinoline-4-carboxamide | |
| 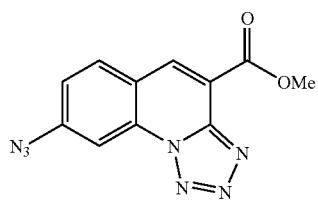 | methyl 8-azido-tetrazolo[1,5-a]quinoline 4-carboxylate | |
| 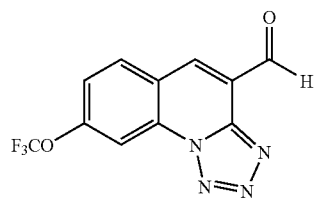 | 8-(trifluoro-methoxy)-tetrazolo[1,5-a]quinoline-4-carbaldehyde | |
| 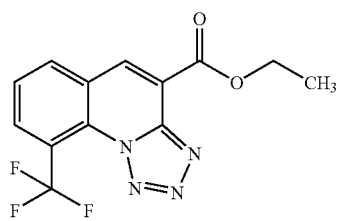 | ethyl 9-(trifluoro-methyl)-tetrazolo[1,5-a]quinoline-4-carboxylate | |
| 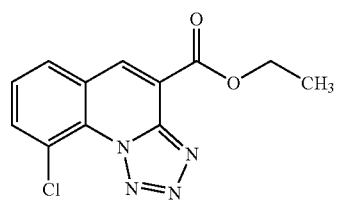 | ethyl 9-chloro-tetrazolo[1,5-a]quinoline-4-carboxylate | |
| 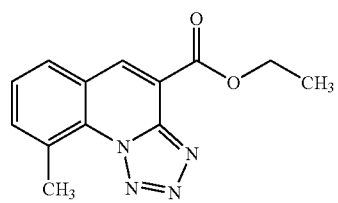 | ethyl 9-methyl-tetrazolo[1,5-a]quinoline-4-carboxylate | |
| 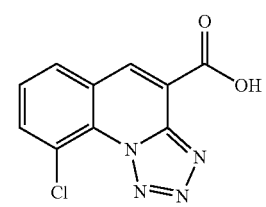 | 9-chloro-tetrazolo[1,5-a]quinoline-4-carboxylic acid | |

TABLE 3-continued

| | | |
|---|---|---|
| 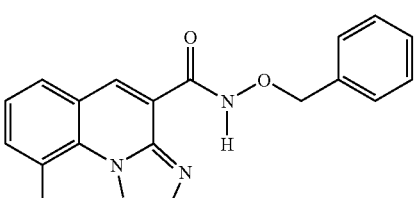 | N-(benzyloxy)-9-chloro-tetrazolo[1,5-a]quinoline 4-carboxamide | |
| 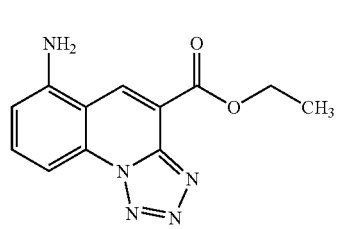 | ethyl 6-amino-tetrazolo[1,5-a]quinoline-4-carboxylate | |
| 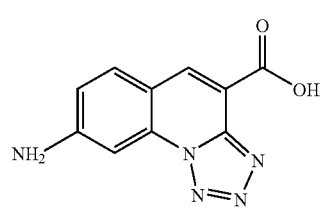 | 8-amino-tetrazolo[1,5-a]quinoline-4-carboxylic acid | |
| 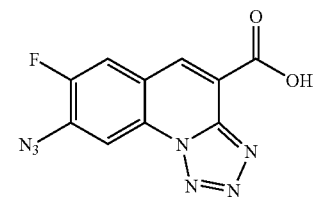 | 8-azido-7-fluoro-tetrazolo[1,5-a]quinoline-4-carboxylic acid | |
| 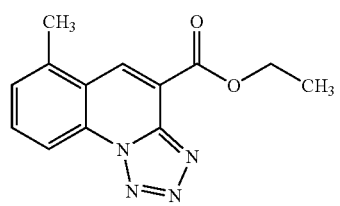 | ethyl 6-methyl-tetrazolo[1,5-a]quinoline-4-carboxylate | |
| 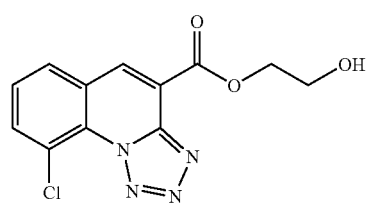 | 2-hydroxyethyl 9-chloro-tetrazolo[1,5-a]quinoline-4-carboxylate | |
| 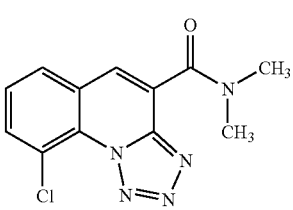 | 9-chloro-N,N-dimethyl-tetrazolo[1,5-a]quinoline-4-carboxamide | |

TABLE 3-continued

| Structure | Name |
|---|---|
| (6-hydroxyhexyl ester, 9-chloro) | 6-hydroxyhexyl 9-chloro-tetrazolo[1,5-a]quinoline-4-carboxylate |
| (ethyl ester, 6-chloro) | ethyl 6-chloro-tetrazolo[1,5-a]quinoline-4-carboxylate |
| (6-chloro carboxylic acid) | 6-chloro-tetrazolo[1,5-a]quinoline-4-carboxylic acid |
| (2-hydroxyethyl ester, 8-CF3) | 2-hydroxyethyl 8-(trifluoromethyl)-tetrazolo[1,5-a]quinoline-4-carboxylate |
| (2-hydroxyethyl ester, 8-OCF3) | 2-hydroxyethyl 8-(trifluoromethoxy)-tetrazolo[1,5-a]quinoline-4-carboxylate |
| (2-methoxyethyl ester, 9-chloro) | 2-methoxyethyl 9-chloro-tetrazolo[1,5-a]quinoline-4-carboxylate |
| (3-hydroxypropyl ester, 9-chloro) | 3-hydroxypropyl 9-chloro-tetrazolo[1,5-a]quinoline-4-carboxylate |
| (2-cyanoethyl ester, 9-chloro) | 2-cyanoethyl 9-chloro-tetrazolo[1,5-a]quinoline-4-carboxylate |
| (8,9-dimethoxy carbaldehyde) | 8,9-dimethoxy-tetrazolo[1,5-a]quinoline-4-carbaldehyde |
| (N-benzyl methanamine, 8-chloro) | N-benzyl-1-(8-chloro-tetrazolo[1,5-a]quinolin-4-yl)-methanamine |
| (8-chloro-4-(1,3-dioxolan-2-yl)) | 8-chloro-4-(1,3-dioxolan-2-yl)tetrazolo[1,5-a]-quinoline |
| (8-chloro-4-(4,4-dimethyloxazoline)) | 8-chloro-4-(4',4'-dimethyl-4',5'-dihydro-1',3'-oxazol-2'-yl)tetrazolo[1,5-a]quinoline |
| (8-chloro-N-methyl carboxamide) | 8-chloro-N-methyl-tetrazolo[1,5-a]quinoline-4-carboxamide |
| (ethyl ester, 8-nitro) | ethyl 8-nitro-tetrazolo[1,5-a]quinoline-4-carboxylate |

TABLE 3-continued

| Structure | Name |
|---|---|
| 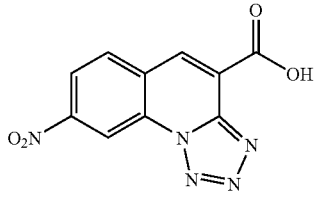 | 8-nitro-tetrazolo[1,5-a]quinoline-4-carboxylic acid |
| 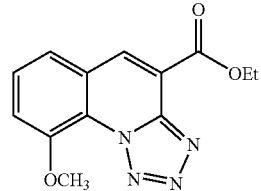 | ethyl 9-methoxy-tetrazolo[1,5-a]quinoline-4-carboxylate |
| 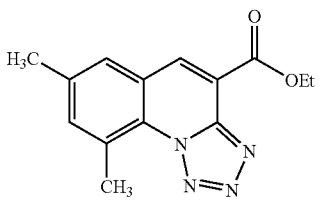 | ethyl 7,9-dimethyl-tetrazolo[1,5-a]quinoline-4-carboxylate |
| 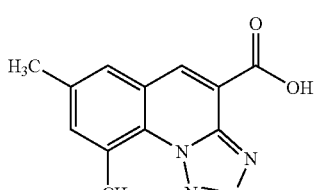 | 7,9-dimethyl-tetrazolo[1,5-a]quinoline-4-carboxylic acid |
| 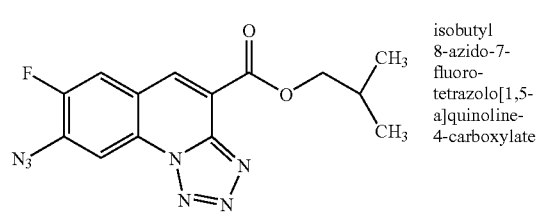 | isobutyl 8-azido-7-fluoro-tetrazolo[1,5-a]quinoline-4-carboxylate |
| 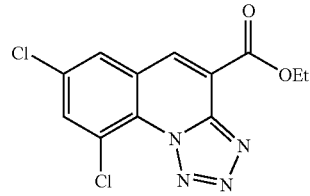 | ethyl 7,9-dichloro-tetrazolo[1,5-a]quinoline-4-carboxylate |

TABLE 3-continued

| Structure | Name |
|---|---|
| 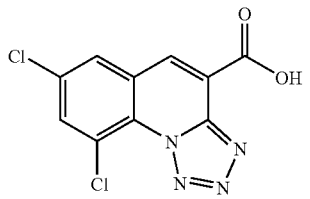 | 7,9-dichloro-tetrazolo[1,5-a]quinoline-4-carboxylic acid |
| 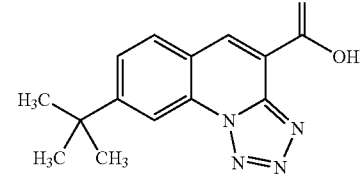 | 8-tert-butyl-tetrazolo[1,5-a]quinoline-4-carboxylic acid |
| 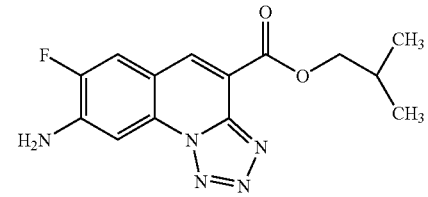 | isobutyl 8-amino-7-fluoro-tetrazolo[1,5-a]quinoline-4-carboxylate |
| 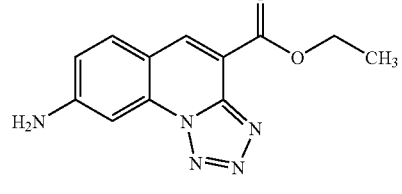 | ethyl 8-amino-tetrazolo[1,5-a]quinoline-4-carboxylate |
| 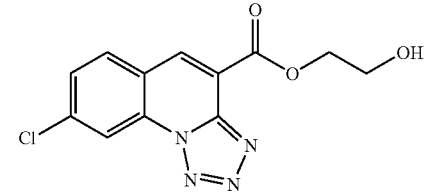 | 2-hydroxyethyl 8-chloro-tetrazolo[1,5-a]quinoline-4-carboxylate |
| 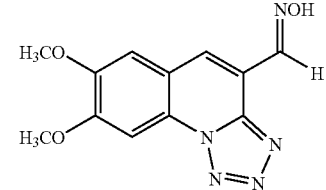 | 4-[(hydroxy-amino)-methyl]-7,8-dimethoxy-tetrazolo[1,5-a]quinoline |
| 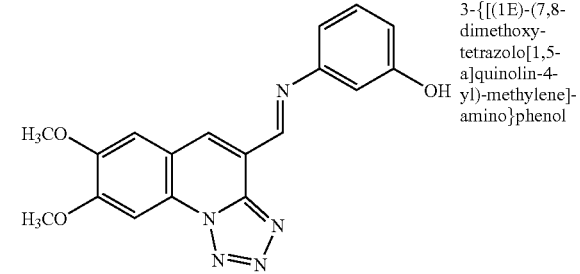 | 3-{[(1E)-(7,8-dimethoxy-tetrazolo[1,5-a]quinolin-4-yl)-methylene]-amino}phenol |

TABLE 3-continued

| Structure | Name |
|---|---|
| (structure shown) | 3-{[(7,8-dimethoxy-tetrazolo[1,5-a]quinolin-4-yl)methyl]-amino}phenol |

The compounds in Table 4 below also exhibit HCV inhibitory activity.

TABLE 4

| Structure | Name | Activity | M − H⁺ |
|---|---|---|---|
| (structure shown) | tetrazolo[1,5-a]thieno[2,3-e]pyridine-4-carboxylic acid | + | 221 |
| (structure shown) | N-(tetrahydro-2H-pyran-2-yloxy)tetrazolo[1,5-a]thieno[2,3-e]-pyridine-4-carboxamide | + | 318 |
| (structure shown) | N-hydroxytetrazolo[1,5-a]thieno[2,3-e]pyridine-4-carboxamide | ++ | 234 |

+ means greater than 20 uM; ++ means 1-20 uM; +++ means lesser than 1 uM

The compounds in Table 5 below inhibit HCV activity from 4% to 110% at a concentration of 3 uM.

TABLE 5

| Structure | Name |
|---|---|
| (structure shown) | tetrazolo[1,5-a]-thieno[2,3-e]pyridine-4-carboxylic acid |
| (structure shown) | N-(tetrahydro-2H-pyran-2-yloxy)tetrazolo[1,5-a]thieno[2,3-e]pyridine-4-carboxamide |
| (structure shown) | N-hydroxytetrazolo[1,5-a]thieno[2,3-e]pyridine-4-carboxamide |
| (structure shown) | tetrazolo[1,5-a]-thieno[2,3-e]-pyridine-4-carbaldehyde |

TABLE 5-continued

| Structure | Name |
|---|---|
| 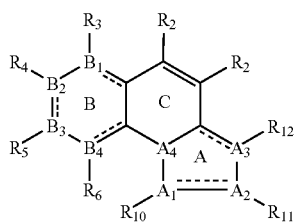 | tetrazolo[1,5-a]-thieno[2,3-e]pyridine-4-carbaldehyde O-methyloxime |

What is claimed is:

1. A compound of formula II, $$\text{II}$$

and pharmaceutically acceptable salts and N-oxides thereof wherein, $R_1$ is, —OH, $C_1$-$C_6$-alkyl, acridinyl, azocinyl, benzimidazolyl, benzofuranyl, benzothiofuranyl, benzothienyl, benzoxazolyl, benzthiazolyl, benztriazolyl, benztetrazolyl, benz-1H-tetrazolyl, benz-2H-tetrazolyl, benz-3H-tetrazolyl, benz-4H-tetrazolyl, benz-5H-tetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3 -oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3 ,4-triazolyl, benzodiazepinyl, xanthenyl, $C_1$-$C_6$-alkyl-$OR_7$, $C_1$-$C_6$-alkyl-OH, aryl, halogen, cyano, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—N($R_7$)—$OR_7$, —CO—$R_7$,$C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl -$NR_7$—$OR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —$SO_2R_7$, —$SOR_7$, —$SO_2NH_2$, —$SO_2NHR_7$, —$SO_2NR_7R_7$, —$SO_2$-heteroaryl, —$SO_2$-aryl, —$SO_3H$, —$SO_3R_7$, —$SO_2Cl$, —$NHR_7$,$C_1$-$C_6$alkyl-NH($R_7$)-aryl,$C_1$-$C_6$-alkyl-$NR_7$—$OR_7$, —NH($R_7$)-aryl, —CO-heteroaryl, —NH—CO—O—$R_7$-aryl, —NH—CO—NH—$SO_2$-aryl, —NH—CO—$OR_7$, —NH—CO—NH—($C_1$-$C_6$-alkyl) or —NH—CO—($C_1$-$C_6$-alkyl), wherein each of the alkyl, heterocyclyl, heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen;

each of $R_2$, $R_4$, and $R_5$ is independently selected from hydrogen, nitro, —OH, $C_1$-$C_6$-alkyl, heterocyclyl, —O-halo($C_1$-$C_6$-alkyl), halo($C_1$-$C_6$alkyl), $C_1$-$C_6$-alkyl-$OR_7$, $C_1$-$C_6$-alkyl-OH, aryl, heteroaryl, heterocyclic, halogen, cyano, —$OCF_3$, —$CF_3$, azido, —O—($C_3$-$C_6$-cycloalkyl), —S—($C_1$-$C_6$-alkyl), $C_1$-$C_6$-alkoxy, —($C_1$-$C_6$-alkoxy)-aryl, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—N($R_7$)—$OR_7$, —CO—$R_7$, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —$SO_2R_7$, —$SOR_7$, —$SO_2NH_2$, —$SO_2NHR_7$, —$SO_2NR_7R_7$, —$SO_2$-heteroaryl, —$SO_2$-aryl, —$SO_3H$, —$SO_3R_7$, —$SO_2Cl$, —$NH_2$, —$NHR_7$, —$NR_7R_7$, $C_1$-$C_6$alkyl-NH($R_7$)—aryl, $C_1$-$C_6$-alkyl-$NR_7$—$OR_7$, —NH($R_7$)-aryl, —CO-heteroaryl, —N($R_7$)—CO-$R_7$, —NH—$SO_2$—$R_7$, —N($R_7$)—CO—$NR_7R_7$, —NH—CO—O—$R_7$-aryl, —NH—CO—NH—$SO_2$-aryl, —$NR_7$—CO—$OR_7$, —NH—CO—$OR_7$, —NH—CO—NH—($C_1$-$C_6$-alkyl) or —NH—CO—($C_1$-$C_6$-alkyl), wherein each of the alkyl, heterocyclyl, heteroaryl and aryl groups are optionally substituted with $C_1$-$C_6$-alkyl, nitro, hydroxy, $C_1$-$C_6$-alkoxy, —CO—O—($C_1$-$C_6$akyl), cyano, —O-halo($C_1$-$C_6$-alkyl), halo($C_1$-$C_6$-alkyl) or halogen; or $R_4$ and $R_5$ together with the carbon atoms to which they are attached form an aryl, heterocyclyl or heteroaryl; or $R_1$ is a group selected from

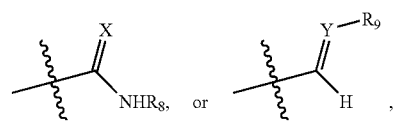

wherein X is =NH or =S, Y is =N—, $R_8$ is hydrogen or hydroxy, $R_9$ is hydroxy, $C_1$-$C_6$-alkoxy or aryl optionally substituted with hydroxy or $C_1$-$C_6$-alkyl; and and $R_2$ is H or a group selected from

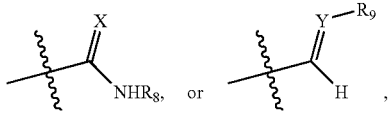

wherein X is =NH or =S, Y is =N—, $R_8$ is hydrogen or hydroxy, $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

each of $R_{10}$, $R_{11}$, and $R_{12}$ is independently selected from hydrogen, —CN, —$NO_2$, —OH, $C_1$-$C_6$-alkyl, aryl, $C_1$-$C_6$-alkyl-aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—$R_7$, —CO—OH, —CO—$OR_7$, —CO—$NH_2$, —CO—$NHR_7$, —CO—$NR_7R_7$, —CO—$N(R_7)OR_7$, —CO—$NR_7OH$, —CO—$NHOR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl-CO—$NR_7OH$, —CO—$N(R_7)OH$, —CO—NHOH, —CO—H, —$SO_2$—$R_7$, —SO—$R_7$, —SO—($C_1$-$C_6$-alkyl), —$SO_2$—($C_1$-$C_6$-alkyl), —$SO_2NH_2$, —$SO_2NHR_7$, —$SO_2NR_7R_7$, —CO—heteroaryl, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $NH_2$, —$NHR_7$, —$NR_7R_7$, —$N(R_7)$—CO—$R_7$, —$NHSO_2R_7$, —$N(R_7)$—CO—$OR_7$ or —$N(R_7)$—CO—$NR_7R_7$, wherein each of the alkyl, alkoxy, aryl, heteroaryl and heterocyclyl are optionally substituted with one or more halogen, $C_1$-$C_6$-alkyl, $C_1$-$C_6$-alkoxy, —$OCF_3$, —$CF_3$, —CN, —$NH_2$, —$NO_2$, —OH, mono- or di- $C_1$-$C_6$-alkylamino, or oxo;

$R_7$ is hydrogen, $C_1$-$C_6$-alkyl, —($C_1$-$C_6$-alkyl)—OH, —($C_1$-$C_6$-alkyl)—O—($C_1$-$C_6$-alkyl), —($C_1$-$C_6$-alkyl)—CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O- halo ($C_1$-$C_6$-alkyl), halo($C_1$-$C_6$alkyl) or halogen;

$A_1$, $A_2$, $A_3$, and $A_4$ are each N;

$B_1$ is S, $B_4$ is a bond, and $B_2$ and $B_3$ are C, the R group attached to $B_1$ and $B_4$, $R_3$ and $R_6$, respectively, are absent and the B ring is a five membered ring; and the dashed lines of rings A, B and C represent single or double bonds such that each annular N has three bonds, each annular O has two bonds, each annular S has two bonds and each annular C has four bonds.

2. A compound according to claim 1 of the formula

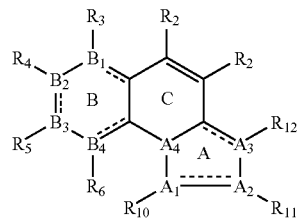

II and pharmaceutically acceptable salts and N-oxides thereof wherein $R_1$ is —OH, $C_1$-$C_6$-alkyl, $C_1$-$C_6$-alkyl-$OR_7$, $C_1$-$C_6$-alkyl-OH, aryl, acridinyl, benzimidazolyl, benzofuranyl, benzothienyl, benzoxazolyl, benzthiazolyl, benztriazolyl, benztetrazolyl, benz-1H-tetrazolyl, benz-2H-tetrazolyl, benz-3H-tetrazolyl, benz-4H-tetrazolyl, benz-5H-tetrazolyl, benzisoxazolyl, benzisothiazolyl, benzimidazolinyl, carbazolyl, 4aH-carbazolyl, carbolinyl, cinnolinyl, furanyl, furazanyl, imidazolyl, 1H-indazolyl, indolizinyl, indolyl, 3H-indolyl, isobenzofuranyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phenanthridinyl, phenanthrolinyl, phenazinyl, phthalazinyl, pteridinyl, purinyl, pyranyl, pyrazinyl, pyrazolyl, pyridazinyl, pyridooxazolyl, pyridoimidazolyl, pyridothiazolyl, pyridinyl, pyridyl, pyrimidinyl, 2H-pyrrolyl, pyrrolyl, quinazolinyl, quinolinyl, 4H-quinolizinyl, quinoxalinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, halogen, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—N($R_7$)—$OR_7$, —CO—$R_7$, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $C_1$-$C_6$-alkyl-CO—$NHOR_7$, $C_1$-$C_6$-alkyl -CO—$NR_7OR_7$, $C_1$-$C_6$-alkyl-CO—NHOH, $C_1$-$C_6$-alkyl—CO—$NR_7OH$, —$SO_2R_7$, —$SOR_7$, —$SO_2NH_2$, —$SO_2NHR_7$, —$SO_2NR_7R_7$, —$SO_2$heteroaryl, —$SO_2$-aryl, —$SO_3H$, —$SO_3R_7$, —$SO_2Cl$, —$SO_2NHR_7$, —$SO_2N(R_7)$, —$NHR_7$, $C_1$-$C_6$alkyl-NH($R_7$)-aryl, $C_1$-$C_6$-alkyl-$NR_7$—$OR_7$, —NH($R_7$)-aryl, —CO—heteroaryl, —NH—CO—O—$R_7$-aryl, —NH—CO—NH—$SO_2$-aryl, —NH—CO—$OR_7$, —NH—CO—NH—($C_1$-$C_6$-alkyl) or —NH—CO—( $C_1$-$C_6$-alkyl), wherein each of the alkyl, heterocyclyl, heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) halogen;

$R_2$ is hydrogen, —OH, $C_1$-$C_6$-alkyl, $C_1$-$C_6$-alkyl-$OR_7$, $C_1$-$C_6$-alkyl-OH, aryl, heteroaryl, halogen, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—$NR_7$—OH, —CO—N($R_7$)—$OR_7$, —CO—$R_7$, $C_1$-$C_6$-alkyl-NH—$OR_7$, $C_1$-$C_6$-alkyl-NH—OH, $C_1$-$C_6$-alkyl-$NR_7$—OH, $C_1$-$C_6$-alkyl-$NR_7$—$OR_7$, $C_1$-$C_6$-alkyl-CO—$NHOR_7$, $C_1$-$C_6$-alkyl-CO—$NR_7OR_7$, $C_1$-$C_6$-alkyl-CO—NHOH, $C_1$-$C_6$-alkyl- CO—NR$_7$OH, —SO$_2$R$_7$, —SOR$_7$, —SO$_2$NH$_2$, —SO$_2$NHR$_7$, —SO$_2$NR$_7$R$_7$, —SO$_2$heteroaryl, —SO$_2$-aryl, —SO$_3$H, —SO$_3$R$_7$, —SO$_2$Cl, —SO$_2$NHR$_7$, —SO$_2$N(R$_7$), —NHR$_7$, C$_1$C$_6$alkyl-NH(R$_7$)-aryl, C$_1$-C$_6$-alkyl-NR$_7$—OR$_7$, —NH(R$_7$)-aryl, —CO-heteroaryl, —NH—CO—O—R$_7$-aryl, —NH—CO—NH—SO$_2$-aryl, —NH—CO—OR$_7$, —NH—CO—NH—(C$_1$-C$_6$-alkyl) or —NH—CO—(C$_1$-C$_6$-alkyl), wherein each of the alkyl, heterocyclyl, heteroaryl and aryl groups are optionally substituted with C$_1$-C$_6$-alkyl, nitro, hydroxy, C$_1$-C$_6$-alkoxy, —CO—O—(C$_1$-C$_6$-akyl), cyano, —O- halo(C$_1$-C$_6$-alkyl), halo(C$_1$-C$_6$-alkyl) or halogen; or

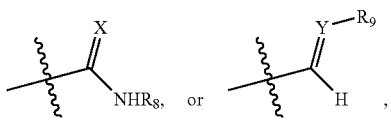

wherein X is =NH or S, Y is =N—, R$_8$ is hydrogen or hydroxy, R$_9$ is hydroxy, C$_1$-C$_6$-alkoxy or aryl optionally substituted with hydroxy or C$_1$-C$_6$-alkyl; or R$_4$, and R$_5$ are independently hydrogen, nitro, C$_1$-C$_6$-alkyl, aryl, —O-halo(C$_1$-C$_6$-alkyl), halo(C$_1$-C$_6$-alkyl), —O—(C$_3$-C$_6$-cycloalkyl), —S—(C$_1$-C$_6$-alkyl), —SO—(C$_1$-C$_6$-alkyl), —SO$_2$—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —CO—NHOH, —CO—NHOR$_7$, —CO—NR$_7$OH, —CO—NR$_7$OR$_7$, —SO$_2$—(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO-R$_7$, —NHSO$_2$R$_7$, —N(R$_7$)—CO—OR$_7$, —N(R$_7$)—CO—NR$_7$R$_7$, R$_4$ and R$_5$ together with the carbon atoms to which they are attached form a heteroaryl;

R$_7$ is hydrogen, C$_1$-C$_6$-alkyl, —(C$_1$-C$_6$-alkyl)—OH, —(C$_1$-C$_6$-alkyl)—O—(C$_1$-C$_6$alkyl), —(C$_1$-C$_6$-alkyl)—CN, C$_2$-C$_6$-alkene, heterocyclyl, aryl, heteroaryl or —(C$_1$-C$_6$-alkyl)-aryl, wherein each of the aryl, heterocyclyl and heteroaryl groups are optionally substituted with C$_1$-C$_6$-alkyl, nitro, hydroxy, C$_1$-C$_6$-alkoxy, —CO—O—(C$_1$-C$_6$-alkyl), cyano, —O— halo(C$_1$-C$_6$-alkyl), halo(C$_1$-C$_6$-alkyl) or halogen;

R$_{10}$, R$_{11}$, and R$_{12}$ are independently hydrogen, —CN, —NO$_2$, —OH, C$_1$-C$_6$-alkyl, aryl, C$_1$-C$_6$-alkyl-aryl, —O-halo(C$_1$-C$_6$-alkyl), halo(C$_1$-C$_6$-alkyl), —O—(C$_3$-C$_6$-cycloalkyl), —S—(C$_1$-C$_6$-alkyl), —SO—(C$_1$-C$_6$-alkyl), —SO$_2$—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—R$_7$, —CO—OH, —CO—OR$_7$, —CO—NH$_2$, —CO—NHR$_7$, —CO—NR$_7$R$_7$, —CO—N(R$_7$)OR$_7$, —CO—NHOR$_7$, C$_1$-C$_6$-alkyl-CO—NHOR$_7$, C$_1$-C$_6$-alkyl-CO—NR$_7$OR$_7$, C$_1$-C$_6$-alkyl-CO—NHOH, C$_1$-C$_6$-alkyl-CO—NR$_7$OH, —CO—N(R$_7$)OH, —CO—NHOH, —CO—H, —SO$_2$—R$_7$, —SO—R$_7$, —SO$_2$—(C$_1$-C$_6$-alkyl), —SO$_2$NH$_2$, —SO$_2$NHR$_7$, —SO$_2$NR$_7$R$_7$, —CO- heteroaryl, C$_1$-C$_6$-alkyl-NH—OR$_7$, C$_1$-C$_6$-alkyl-NH—OH, C$_1$-C$_6$-alkyl-NR$_7$—OH, C$_1$-C$_6$-alkyl-NR$_7$—OR$_7$, NH$_2$, —NHR$_7$, —NR$_7$R$_7$, —N(R$_7$)—CO—R$_7$, —NHSO$_2$R$_7$, —N(R$_7$)—CO—OR$_7$ or —N(R$_7$)—CO—NR$_7$R$_7$, wherein each of the alkyl, alkoxy, aryl, heteroaryl and heterocyclyl are optionally substituted with one or more halogen, C$_1$-C$_6$-alkyl, C$_1$-C$_6$-alkoxy, —OCF$_3$, —CF$_3$, —CN, —NH$_2$, —NO$_2$, —OH, mono- or di- C$_1$-C$_6$-alkylamino, or oxo.

3. The compound according to claim 2 wherein the dashed lines of ring B are independently single or double bonds such that the annular S has two bonds and each annular C has four bonds; R2,R4, R5 and R$_{10}$ to R$_{12}$ are hydrogen; R$_1$ is

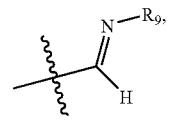

wherein R$_9$ is hydroxy or C$_1$-C$_3$-alkoxy, —CO—H, —CO—OH, —CO—NH—OH, or —CO—NH—OR$_7$, wherein R$_7$ is a heterocyclyl, wherein the heterocyclyl groups is optionally substituted with C$_1$-C$_6$-alkyl, hydroxy, C$_1$-C$_6$-alkoxy, cyano, or halogen.

4. The compound according to claim 3, wherein the R$_9$ is methoxy.

5. The compound according to claim 3 wherein the heterocyclyl is pyranyl.

6. The compound according to claim 5, wherein the heterocyclyl is pyran-2-yl.

7. The compound according to claim 3 that is selected from the group consisting of
tetrazolo[1,5-a]thieno[2,3-e]pyridine-4-carboxylic acid;
N-(tetrahydro-2H-pyran-2-yloxy)tetrazolo[1,5-a]thieno[2,3-e]pyridine-4-carboxamide;
N-hydroxytetrazolo[1,5-a]thieno[2,3-e]pyridine-4-carboxamide;
tetrazolo[1,5-a]thieno[2,3-e]pyridine-4-carbaldehyde;
tetrazolo[1,5-a]thieno[2,3-e]pyridine-4-carbaldehyde O-methyloxime; and
and pharmaceutically acceptable salts and N-oxides thereof.

8. A composition comprising a compound of claim 1 and a pharmaceutically acceptable carder.

9. A method of inhibiting HCV proliferation in vitro comprising contacting an HCV infected cell with a compound according to claim 1.

10. A method of treating a mammal infected with an HCV infection, the method comprising administering to the mammal a therapeutically effective amount of a composition according to claim 8.

11. The method according to claim 10 wherein the mammal is a human.

* * * * *

UNITED STATES PATENT AND TRADEMARK OFFICE
CERTIFICATE OF CORRECTION

PATENT NO. : 7,569,580 B2
APPLICATION NO. : 11/145144
DATED : August 4, 2009
INVENTOR(S) : Thota et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this

Seventh Day of September, 2010

David J. Kappos
*Director of the United States Patent and Trademark Office*